United States Patent
Sakazaki

(10) Patent No.: US 11,420,812 B2
(45) Date of Patent: Aug. 23, 2022

(54) STORAGE CONTAINER, MICRONEEDLE UNIT, STORAGE CONTAINER GROUP, AND METHOD OF PRODUCING MICRONEEDLE UNIT

(71) Applicant: FUJIFILM Corporation, Tokyo (JP)

(72) Inventor: Yoshiki Sakazaki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 353 days.

(21) Appl. No.: 16/833,682

(22) Filed: Mar. 30, 2020

(65) Prior Publication Data

US 2020/0331691 A1 Oct. 22, 2020

(30) Foreign Application Priority Data

Apr. 17, 2019 (JP) .............................. JP2019-078692

(51) Int. Cl.
*A61M 37/00* (2006.01)
*B65D 85/24* (2006.01)
(Continued)

(52) U.S. Cl.
CPC ......... B65D 85/24 (2013.01); A61M 37/0015 (2013.01); A61M 5/002 (2013.01);
(Continued)

(58) Field of Classification Search
CPC ............ A61M 5/3289; A61M 37/0015; A61M 2037/0023; A61M 2037/003;
(Continued)

(56) References Cited

U.S. PATENT DOCUMENTS 6,780,171 B2   8/2004 Gabel et al.
7,156,838 B2   1/2007 Gabel et al.
(Continued)

FOREIGN PATENT DOCUMENTS

CN       108367143    8/2018
JP       4384917      12/2009
(Continued)

OTHER PUBLICATIONS

"Search Report of Europe Counterpart Application", dated Sep. 22, 2020, pp. 1-8.

*Primary Examiner* — Jacob K Ackun
(74) *Attorney, Agent, or Firm* — JCIPRNET

(57) ABSTRACT

Provided are a storage container, a microneedle unit, a storage container group, and a method of producing a microneedle unit that enable protection of a microneedle array before puncture and realization of a puncturing property of the microneedle array using a simple member.
The storage container, which stores a microneedle array including a sheet having a first surface and a second surface that oppose each other and a plurality of needles arranged on the first surface of the sheet, includes a first member having an edge portion that defines a second opening and a second member having a depression, in which the microneedle array is stored by superimposing the second member on the first member, and the second member and the first member are deformed by applying a force to the second member in a state in which the second member is superimposed on the first member, and the needles of the microneedle array are allowed to protrude from the first member to puncture a skin.

16 Claims, 14 Drawing Sheets

(51) Int. Cl.
   *B65D 21/00*      (2006.01)
   *A61M 5/00*       (2006.01)
(52) U.S. Cl.
   CPC .............. *A61M 2037/0023* (2013.01); *A61M 2037/0053* (2013.01); *B65D 21/00* (2013.01)
(58) Field of Classification Search
   CPC .. A61M 2037/0038; A61M 2037/0046; A61M 5/002; B65D 21/00; B65D 85/24
   USPC .......................... 604/890.1, 93.01, 173, 134
   See application file for complete search history.

(56) References Cited

U.S. PATENT DOCUMENTS

| | | |
|---|---|---|
| 8,821,446 B2 | 9/2014 | Trautman et al. |
| 2007/0021717 A1 | 1/2007 | Gabel et al. |
| 2014/0336616 A1 | 11/2014 | Edwards |
| 2016/0121092 A1 | 5/2016 | Kato |
| 2017/0304604 A1 | 10/2017 | Kato |
| 2018/0361132 A1 | 12/2018 | Kobayashi et al. |
| 2019/0351588 A1* | 11/2019 | Sakazaki ........... A61M 37/0015 |
| 2020/0101205 A1* | 4/2020 | Todd .................. A61B 5/15117 |
| 2020/0101274 A1 | 4/2020 | Kobayashi et al. |
| 2022/0072290 A1* | 3/2022 | Kulik ................ A61M 37/0015 |
| 2022/0072292 A1* | 3/2022 | Erlhofer ............ A61M 37/0015 |

FOREIGN PATENT DOCUMENTS

| | | |
|---|---|---|
| JP | 5553612 | 7/2014 |
| JP | 2018102680 | 7/2018 |
| WO | 2016123665 | 8/2016 |
| WO | 2018110510 | 6/2018 |

\* cited by examiner

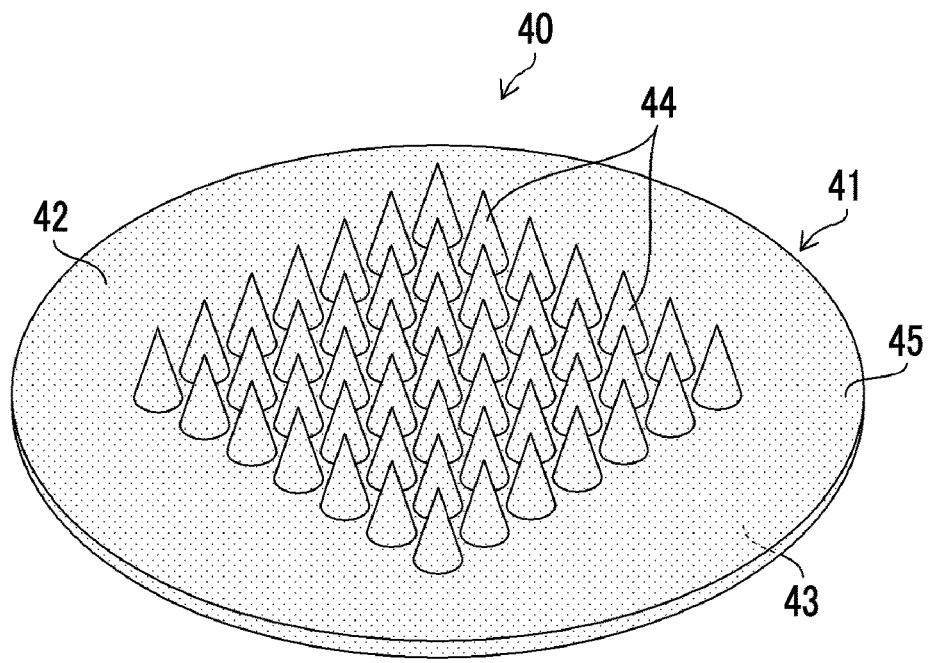
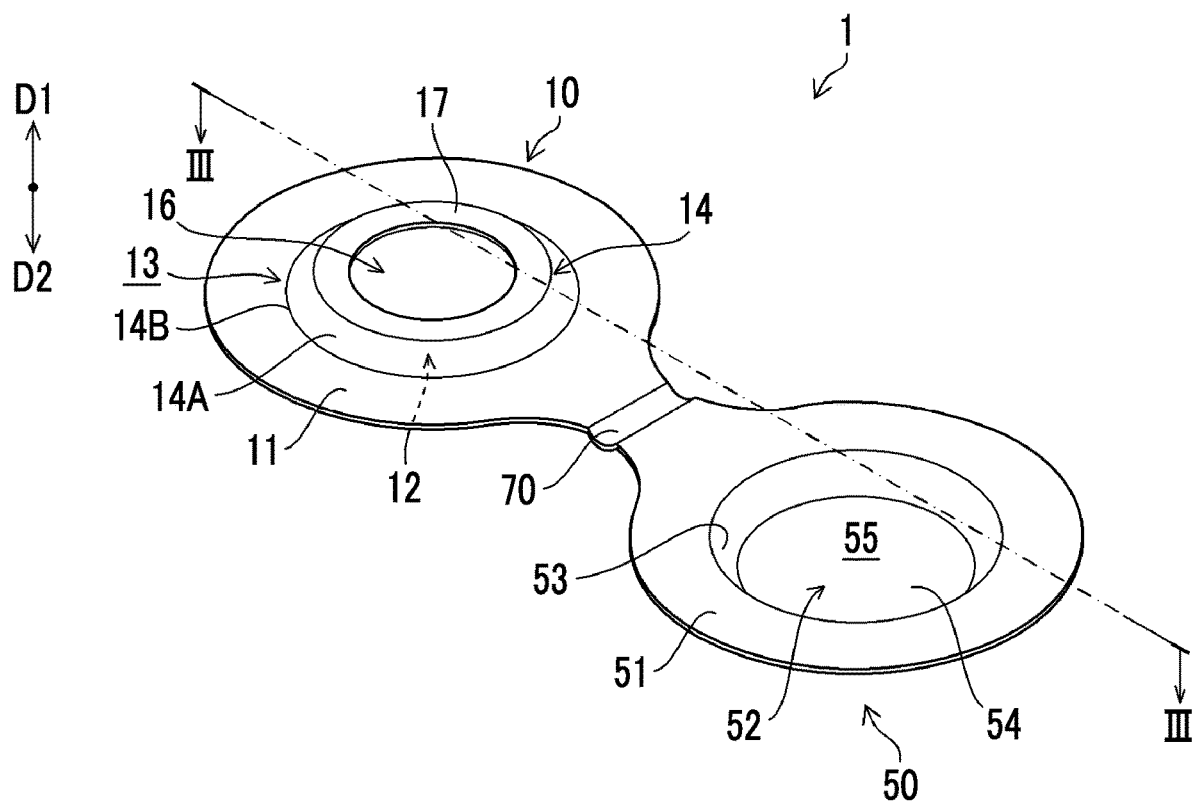

FIG. 5
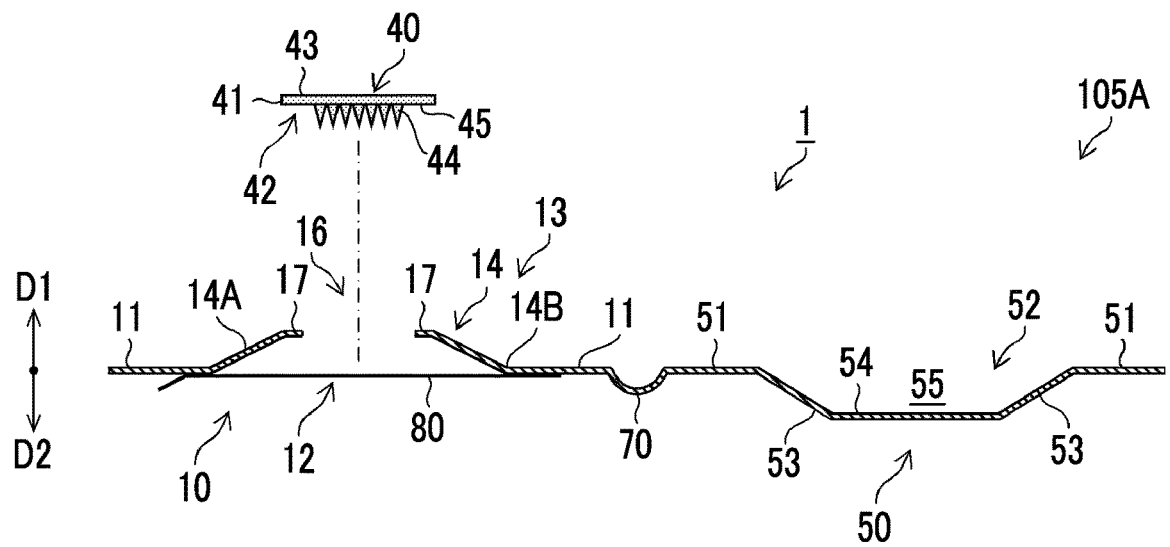
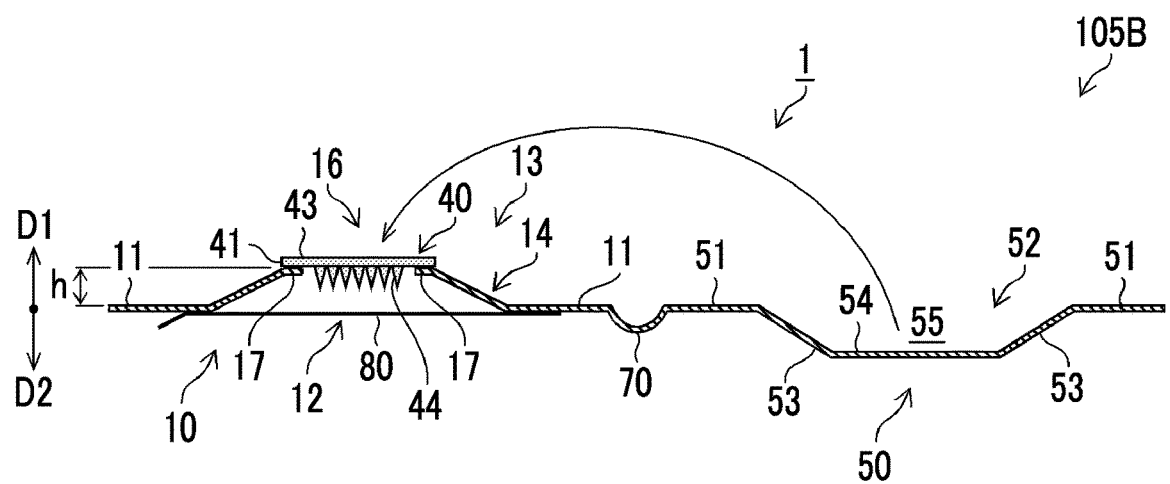
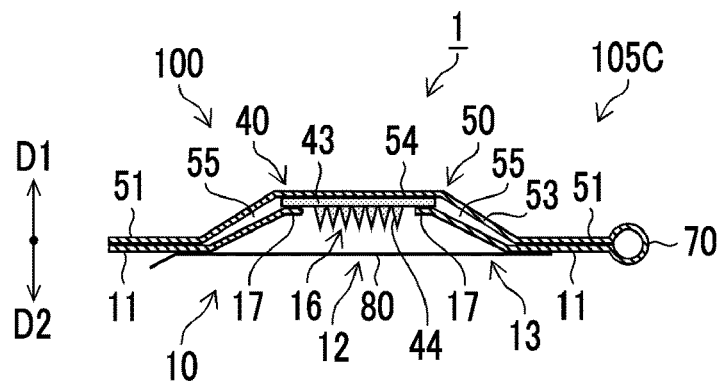

FIG. 7
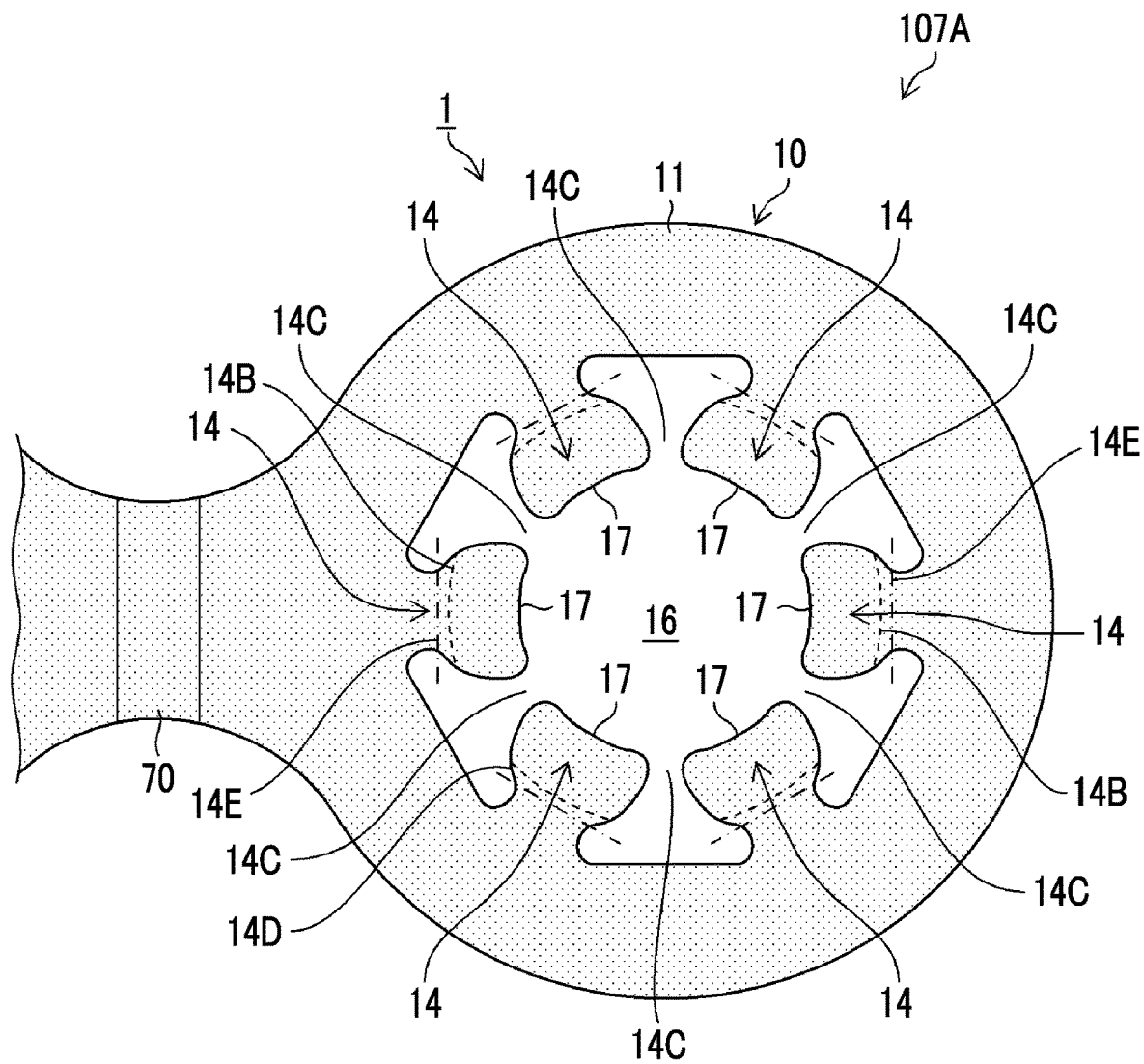
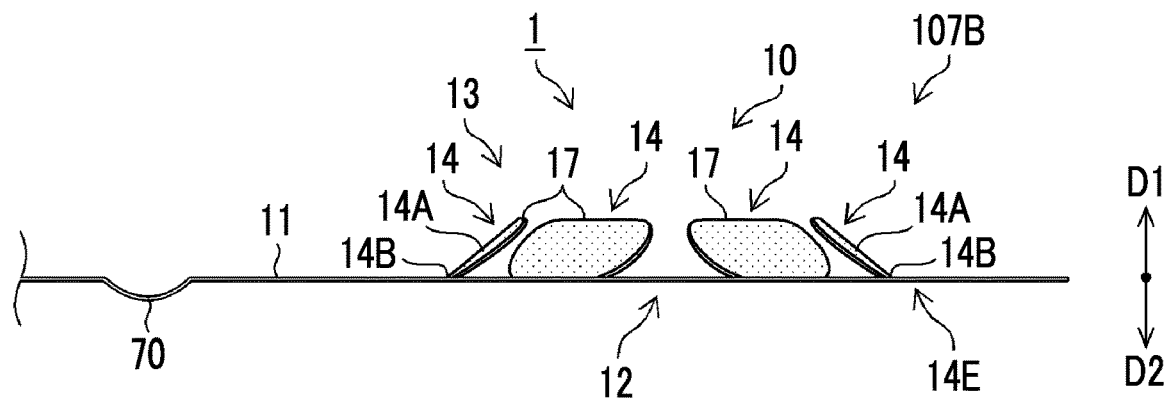

FIG. 8
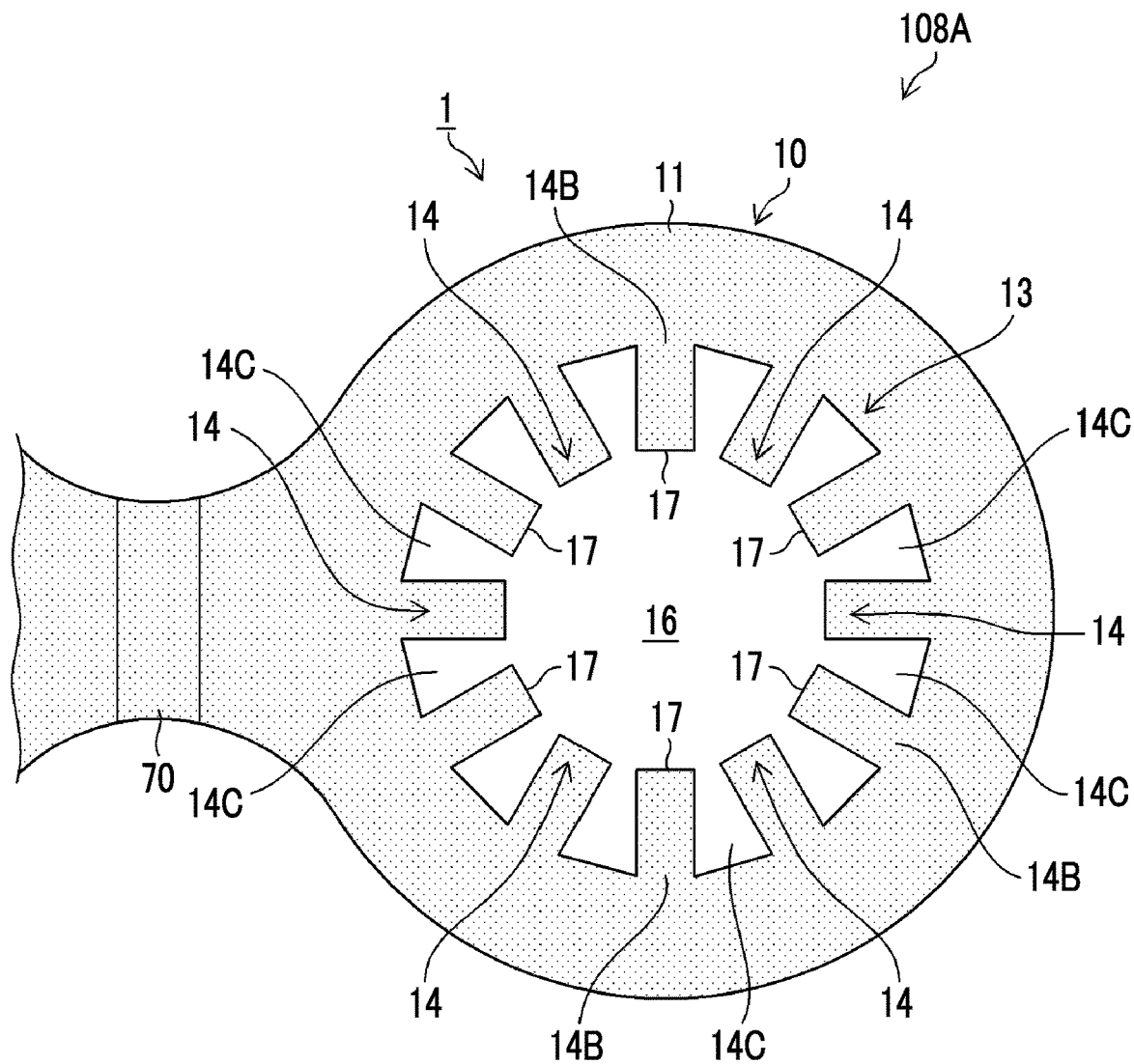
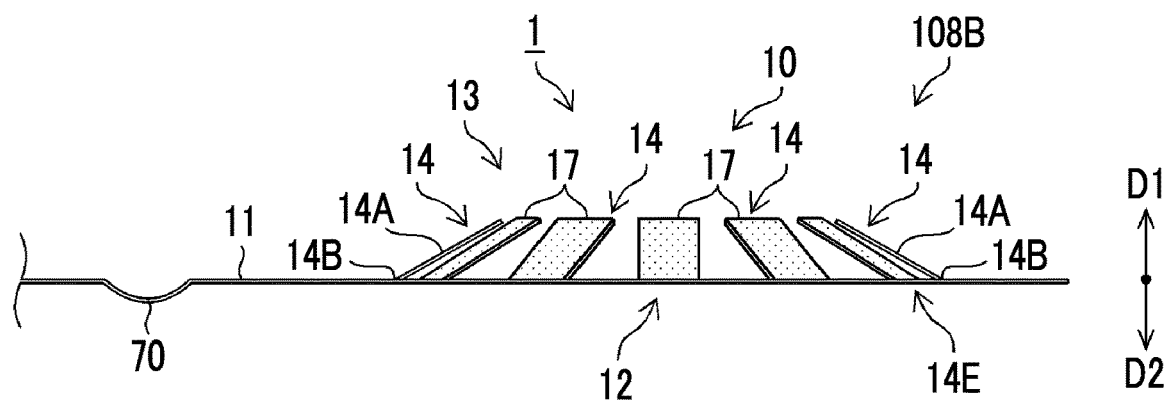

FIG. 9
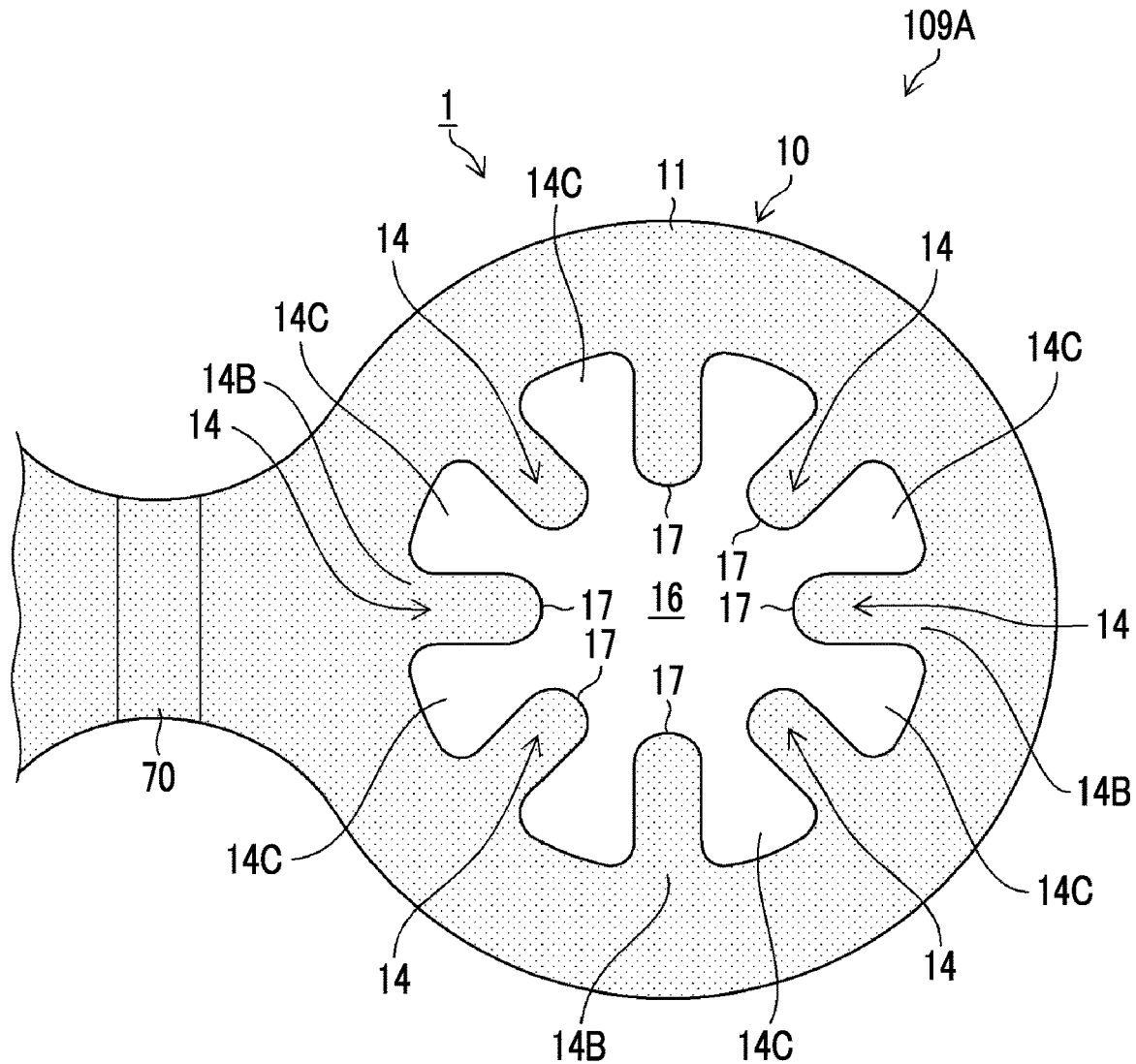
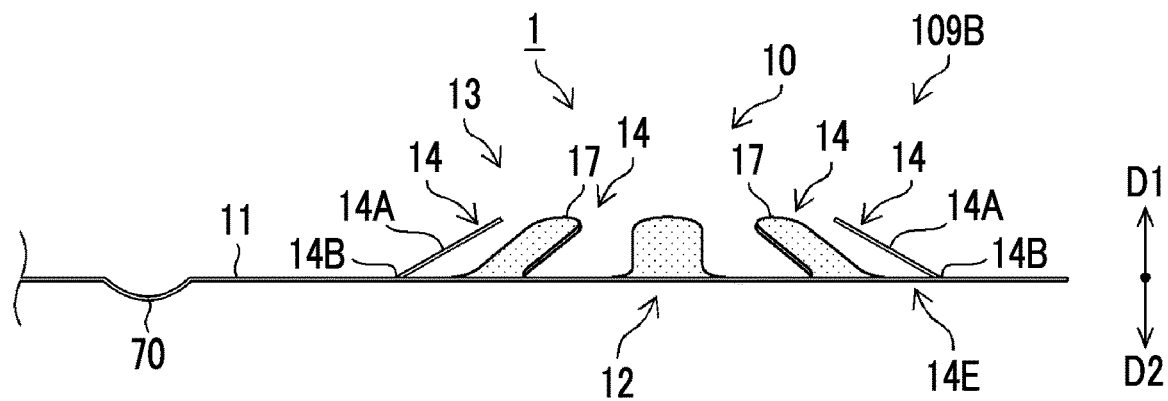

FIG. 12
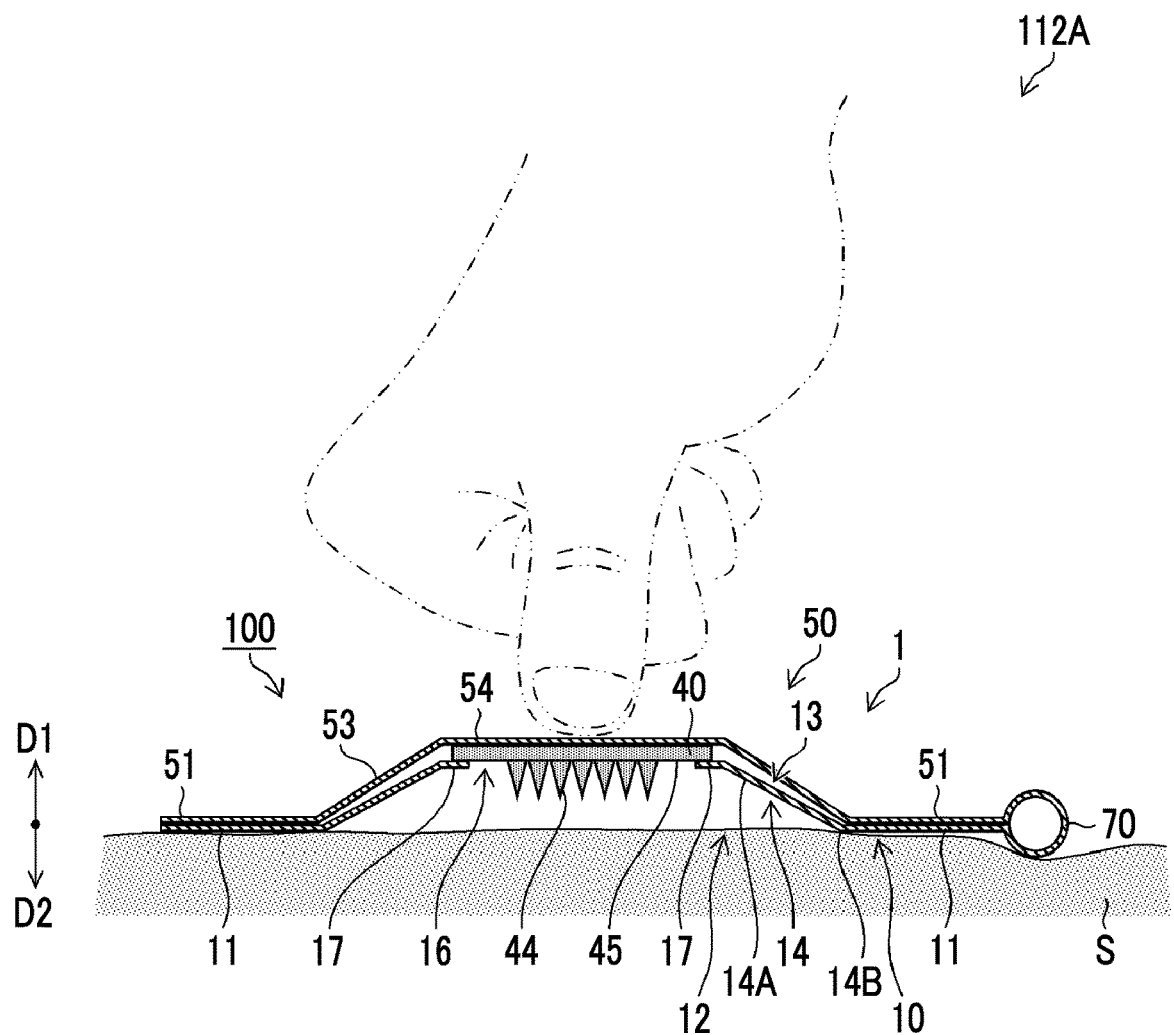
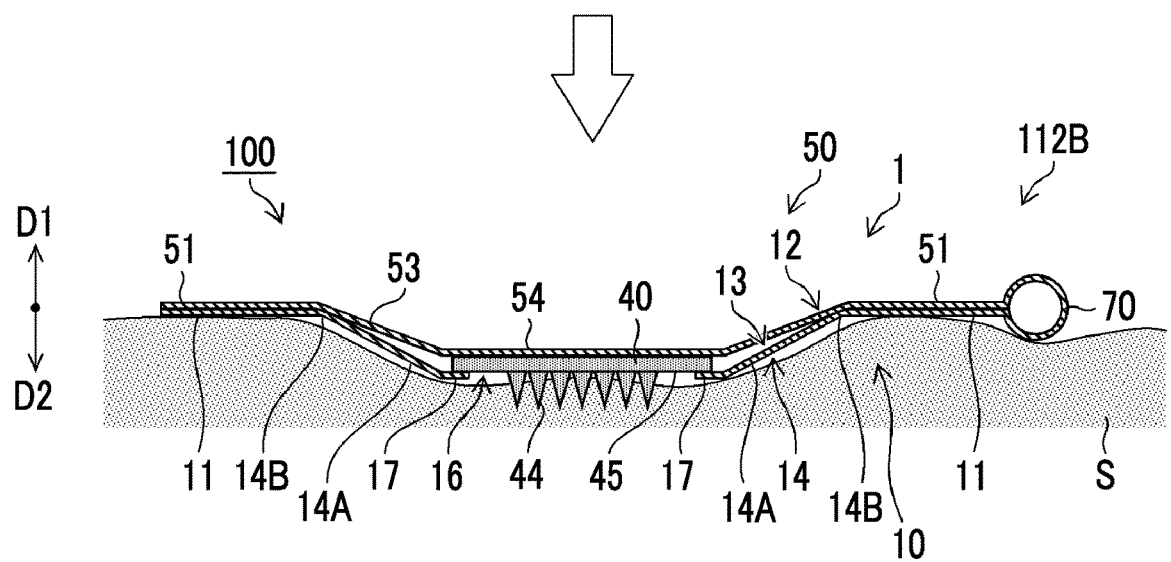

STORAGE CONTAINER, MICRONEEDLE UNIT, STORAGE CONTAINER GROUP, AND METHOD OF PRODUCING MICRONEEDLE UNIT

CROSS-REFERENCE TO RELATED APPLICATION

The present application claims priority under 35 U.S.C § 119(a) to Japanese Patent Application No. 2019-078692 filed on Apr. 17, 2019, which is hereby expressly incorporated by reference, in its entirety, into the present application.

BACKGROUND OF THE INVENTION

1. Field of the Invention

The present invention relates to a storage container, a microneedle unit, a storage container group, and a method of producing a microneedle unit.

2. Description of the Related Art

In recent years, a microneedle array has been known as a new dosage form capable of administering a drug into the skin without pain. The microneedle array is formed of microneedles (also referred to as fine needles or microneedles) containing a drug, which are arranged in an array. By pressing this microneedle array against the skin, the skin is punctured by each microneedle. The drug is absorbed into the skin from the microneedles that have punctured the skin and then administered.

Various applicators have been suggested in order to reliably puncture the microneedle array into the skin. JP5553612B discloses an applicator which has an inner portion and an outer portion and is formed by attaching a microneedle array to a lower surface of the inner portion. JP2018-102680A discloses a puncture kit which comprises an applicator energizing a piston with an elastic member, and a cartridge comprising a microneedle array and being detachable from the applicator.

SUMMARY OF THE INVENTION

In JP5553612B, the microneedle array is attached to the lower surface of the inner portion using an adhesive. However, there is concern for maintenance of the stability of the adhesive during a period of a sterilization operation and long-term storage. In addition, it is necessary to confirm whether components volatilized and eluted from the adhesive cause deterioration of the drug.

In JP2018-102680A, an applicator and a cartridge with complicated mechanisms are used to protect the microneedle array before puncture and achieve a puncturing property of the microneedle array.

The present invention has been made in consideration of the above-described circumstances, and an object thereof is to provide a storage container, a microneedle unit, a storage container group, and a method of producing a microneedle unit that enable protection of a microneedle array before puncture and realization of the puncturing property of the microneedle array using a simple member.

According to a first aspect, there is provided a storage container which stores a microneedle array including a sheet having a first surface and a second surface that oppose each other and a plurality of needles arranged on the first surface of the sheet, the storage container comprising: a first member which includes a first flat portion in which a first opening is formed, and a support portion rising from a peripheral edge of the first opening and defining a second opening with an edge portion and in which an outer peripheral portion where the needles on the sheet of the microneedle array are not arranged is supported by the edge portion of the support portion while allowing the needles of the microneedle array to face the first opening; and a second member which includes a second flat portion in which an opening is formed, a side wall portion rising from a periphery of the opening, and a base connected to the side wall portion and facing the opening and defines a depression with the side wall portion and the base and in which the support portion of the first member is stored in the depression from a side of the second opening by superimposing the second member on the first member, and the microneedle array is stored between the first member and the second member, in which the second member and the first member are deformed by applying a force in a direction of the first member to the second member in a state in which the second member is superimposed on the first member, and the needles of the microneedle array are allowed to protrude from the first member to puncture a skin. In the first aspect, it is possible to protect the microneedle array before puncture and realize the puncturing property of the microneedle array using a simple member.

In the storage container according to a second aspect, the second opening of the support portion has an area that is smaller than the sheet of the microneedle array and larger than a region where the plurality of needles are arranged. In the second aspect, protection of the needles of the microneedle array and support are ensured.

In the storage container according to a third aspect, the first member and the second member are connected through a hinge portion. In the third aspect, the second member can be bent toward the first member.

In the storage container according to a fourth aspect, the first member and the second member have thicknesses different from each other. In the fourth aspect, the relationship between the thickness of the first member and the thickness of the second member constituting the storage container is defined.

In the storage container according to a fifth aspect, a thickness of the first member is smaller than a thickness of the second member. In the fifth aspect, the first member is easily deformed.

In the storage container according to a sixth aspect, a thickness of the first member is in a range of 100 µm to 1000 µm, and a thickness of the second member is in a range of 100 µm to 1000 µm. In the sixth aspect, the preferable thicknesses of the first member and the second member are defined.

In the storage container according to a seventh aspect, the first member includes a penetrating portion formed along a rising portion of the support portion. In the seventh aspect, the force required for deformation of the support portion can be adjusted.

In the storage container according to an eighth aspect, the support portion supports the microneedle array in an inversion state in which the support portion rises in one direction opposite to the other direction from a reference state in which the support portion rises in the other direction, and the support portion is inverted and returns to the reference state upon application of the force to the second member. In the eighth aspect, the microneedle array can stably puncture the skin.

In the storage container according to a ninth aspect, the support portion is formed of a plurality of support members which are separated from one another. In the ninth aspect, the preferable form of the support portion is defined.

In the storage container according to a tenth aspect, the support member includes a constricted portion. In the tenth aspect, the force required for deformation of the support portion is adjusted.

In the storage container according to an eleventh aspect, the support portion has an inclined surface whose diameter is reduced in a rising direction and which is inclined with respect to a puncture surface, and the inclined surface becomes parallel to the puncture surface in a case where the needles of the microneedle array are allowed to protrude from the first member to puncture the skin. In the eleventh aspect, the microneedle array can stably puncture the skin.

According to a twelfth aspect, there is provided a microneedle unit comprising: a microneedle array which includes a sheet having a first surface and a second surface that oppose each other and a plurality of needles arranged inside an outer peripheral portion of the first surface of the sheet; and the storage container described above. In the twelfth aspect, the microneedle unit including the microneedle array and the storage container is defined.

According to a thirteenth aspect, there is provided a storage container group comprising: a plurality of the storage containers described above, in which the storage containers are arranged in one direction by connecting the first members to one another and connecting the second members to one another. In the thirteenth aspect, the storage container group formed of the plurality of the storage containers is defined.

According to a fourteenth aspect, there is provided a storage container group comprising: a plurality of the storage container groups described above, in which the storage container groups are arranged by connecting the first members to one another or the second members to one another. In the fourteenth aspect, the storage container group formed of the plurality of the storage container groups is defined.

According to a fifteenth aspect, there is provided a method of producing a microneedle unit, comprising: preparing a microneedle array which includes a sheet having a first surface and a second surface that oppose each other and a plurality of needles arranged inside an outer peripheral portion of the first surface of the sheet; preparing a storage container which includes a first member including a first flat portion in which a first opening is formed and a support portion rising from a peripheral edge of the first opening in a first direction and defining a second opening with an edge portion, and a second member which includes a second flat portion in which an opening is formed, a side wall portion rising from a periphery of the opening, and a base connected to the side wall portion and facing the opening and defines a depression with the side wall portion and the base; supporting the outer peripheral portion of the microneedle array with the edge portion of the support portion while allowing the needles of the microneedle array to face the first opening; and storing the support portion of the first member and the microneedle array in the depression of the second member from a side of the second opening by superimposing the second member on the first member. In the fifteenth aspect, the method of producing a microneedle unit using the above-described storage container is defined.

According to a sixteenth aspect, there is provided a method of producing a microneedle unit, comprising: preparing a microneedle array which includes a sheet having a first surface and a second surface that oppose each other and a plurality of needles arranged inside an outer peripheral portion of the first surface of the sheet; preparing a storage container which includes a first member including a first flat portion in which a first opening is formed and a support portion rising from a peripheral edge of the first opening in a first direction and defining a second opening with an edge portion, and a second member which includes a second flat portion in which an opening is formed, a side wall portion rising from a periphery of the opening, and a base connected to the side wall portion and facing the opening and defines a depression with the side wall portion and the base; placing the microneedle array on the base while allowing the second surface of the microneedle array to face the base; and storing the support portion in the depression by superimposing the first member on the second member so that the outer peripheral portion of the microneedle array is supported by the edge portion of the support portion. In the sixteenth aspect, the method of producing a microneedle unit using the above-described storage container is defined.

According to the present invention, it is possible to protect the microneedle array before puncture and realize the puncturing property of the microneedle array using a simple member.

BRIEF DESCRIPTION OF THE DRAWINGS

FIG. 1 is a perspective view illustrating a microneedle array.

FIG. 2 is a perspective view illustrating a storage container.

FIG. 5 is an explanatory view illustrating a procedure for storing the microneedle array in the storage container.

FIG. 7 is an explanatory view for explaining the shape of another support portion.

FIG. 8 is an explanatory view for explaining another shape of a support portion.

FIG. 9 is an explanatory view for explaining another shape of the support portion.

FIG. 12 is an explanatory view illustrating a procedure for puncturing the microneedle array.

DESCRIPTION OF THE PREFERRED EMBODIMENTS

Figure 3:
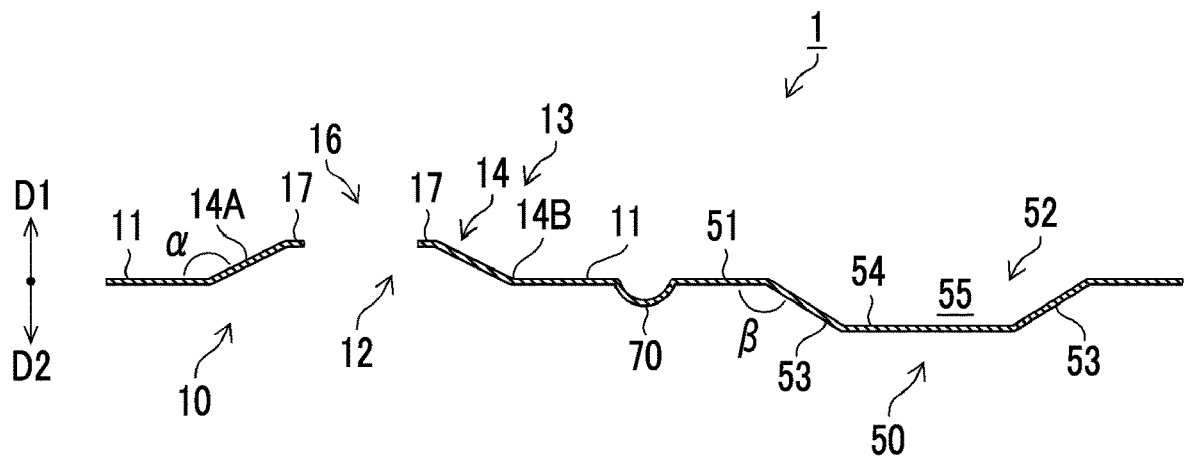
FIG. 3 is a cross-sectional view taken along the line III-III of FIG. 2.

Hereinafter, preferred embodiments of the present invention will be described with reference to the accompanying drawings. The present invention will be described based on the following preferred embodiments. Modifications can be made by various methods without departing from the scope of the invention, and other embodiments other than the embodiments can be used. Accordingly, all modifications within the scope of the present invention are included in the claims. In this specification, "down" is the direction of the gravity, and "up" is the direction opposite to the direction of the gravity.

A typical structure of a microneedle array 40 will be described with reference to FIG. 1. FIG. 1 is a perspective view of the microneedle array 40 for one dose. As illustrated in FIG. 1, the microneedle array 40 includes a sheet 41 having a first surface 42 and a second surface 43 that oppose each other and a plurality of needles 44 arranged on the first surface 42 of the sheet 41. The needles 44 form microneedles. The region in the first surface 42 where the plurality of needles 44 are not arranged forms an outer peripheral portion 45. In the embodiment, the sheet 41 has a circular shape in a plan view. However, the shape of the sheet 41 is not particularly limited and may be rectangular. Here, the plan view indicates a state in which the sheet 41 is observed in a direction orthogonal to the first surface 42.

The shape, the size, and the like of the sheet 41 and the needles 44 are determined depending on the use of the microneedle array 40. Further, the sheet 41 and the needles 44 may be formed of the same material or materials different from each other. The microneedle array 40 can be produced by integrally molding the sheet 41 and the needles 44 or can be separately molded.

In the embodiment, the needles 44 have, for example, a substantially conical shape. The shape of the needles 44 is not particularly limited and may be a polygonal pyramid shape (a quadrangular pyramid shape or the like). Further, the needles 44 may have a multi-stage shape in which a frustum and a cone are combined.

The plurality of needles 44 are arranged on the first surface 42 of the sheet 41 in a predetermined pattern. The pattern can be formed by arranging the plurality of needles 44 concentrically or arranging the plurality of needles 44 in a lattice form. The pattern is not particularly limited and can be appropriately changed.

The plurality of needles 44 are formed of, for example, 4 to 2500 needles 44. Here, the number of the needles 44 is not limited to this number.

It is preferable that the needles 44 is formed of a material that is dissolved after puncture into the skin or the mucous membrane and inserted into the body. As a material constituting the needles 44, a water-soluble polymer is preferable, and polysaccharides are more preferable. It is preferable that the material constituting the needles 44 is formed of at least one selected from the group consisting of hydroxyethyl starch, dextran, chondroitin sulfate, sodium hyaluronate, carboxymethyl cellulose, polyvinylpyrrolidone, polyoxyethylene polyoxypropylene glycol, and polyethylene glycol.

A drug is applied to or contained in the needles 44. The puncture of each needle 44 into the body is carried out by penetrating the needles through the skin at the time of attachment of the sheet 41 to the surface of the skin. In a case where the needles 44 are coated with the drug, the drug is administered into the body from the surface of each needle 44. Further, in a case where each needle 44 contains the drug, since the needles 44 are formed of a material that is dissolved after puncture of the needles into the body, the drug of the needles 44 is administered to the body by the dissolution of the needles 44 in the body.

The drug is not limited as long as the drug has a function as a drug. In particular, it is preferable that the drug is selected from pharmaceutical compounds belonging to peptides, proteins, nucleic acids, polysaccharides, vaccines, and water-soluble low-molecular-weight compounds.

In a case where the sheet 41 of the microneedle array 40 has a circular shape, the diameter thereof is in a range of 10 mm to 30 mm. The sheet 41 has a thickness of 0.1 mm to 5 mm. Further, each needle 44 has a height of, for example, 0.05 mm to 3 mm, more preferably 0.1 mm to 1.5 mm, and still more preferably 0.15 mm to 1 mm. The height is a length from the first surface 42 to the tip of each needle 44.

The interval between the needles 44 is preferably in a range of 0.1 mm to 10 mm, more preferably in a range of 0.2 mm to 5 mm, and still more preferably in a range of 0.3 mm to 3 mm. However, each numerical value of the microneedle array 40 is not limited to the above values. In a step of preparing the microneedle array, for example, the microneedle array 40 having the above-described structure is prepared.

Next, a storage container that stores the microneedle array will be described with reference to FIGS. 2 and 3. A storage container 1 includes a first member 10 and a second member 50. The first member 10 comprises a first flat portion 11 in which a first opening 12 is formed. The first flat portion 11 has a thickness of, for example, 100 μm or more and 1000 μm or less and is formed in a plate shape. The first flat portion 11 may have a flat or substantially flat shape.

The first member 10 comprises a support portion 13 which rises from a peripheral edge of the first opening 12 in a first direction D1 and defines a second opening 16 with an edge portion 17. The support portion 13 is formed of a single support member 14 having an inclined surface 14A whose diameter is reduced from a rising portion 14B in the first direction D1. Since the inclined surface 14A is formed in an annular shape, the support portion 13 has a hollow structure in which the first opening 12 and the second opening 16 communicate with each other. The first direction D1 is a direction orthogonal to the first flat portion 11, and a direction opposite to the first direction D1 is a second direction D2. A direction to be set as the first direction D1 with respect to the first flat portion 11 can be optionally determined. In the embodiment, the first direction D1 is an upward direction, and the second direction D2 means a downward direction.

Since the support portion 13 is formed to rise from the first flat portion 11, an angle α between the first flat portion 11 and the support portion 13 is less than 180°. The angle α is preferably in a range of 90° to 165°. The thickness of the support portion 13 is basically the same as the thickness of the first flat portion 11. The thickness of the first member 10 is represented by the thickness of the first flat portion 11.

The edge portion 17 of the support portion 13 is formed of a flat surface substantially parallel to the first flat portion 11.

The second member 50 includes a second flat portion 51 in which an opening 52 is formed. The second flat portion 51 has a thickness of, for example, 100 μm to 1000 μm and has a plate shape. The second flat portion 51 may have a flat or substantially flat shape.

The second member 50 includes a side wall portion 53 rising from the periphery of the opening 52, and a base 54 connected to the side wall portion 53 and facing the opening 52. The side wall portion 53 is formed in an annular shape and surrounds the whole circumference of the opening 52. A depression 55 defined by the side wall portion 53 and the base 54 is formed in the second member 50.

Since the side wall portion 53 is formed to rise from the second flat portion 51, an angle β between the second flat portion 51 and the side wall portion 53 is less than 180°. The angle β is preferably in a range of 90° to 165°. The thickness of the side wall portion 53 is basically the same as the thickness of the second flat portion 51. The thickness of the second member 50 is represented by the thickness of the second flat portion 51.

The storage container 1 as illustrated in FIGS. 2 and 3 is formed such that the first member 10 and the second member 50 are connected through a hinge portion 70. As illustrated in FIG. 3, the hinge portion 70 has a semicircular shape in a cross-sectional view. The hinge portion 70 enables bending of the second member 50 at the time of bending the second member toward the first member 10 and superimposing the second member 50 on the first member 10. The shape of the hinge portion 70 is not limited as long as the second member 50 can be bent toward the first member 10 and superimposed on the first member 10.

In the embodiment, the storage container 1 is formed such that the first member 10 and the second member 50 are connected through the hinge portion 70, but the first member 10 and the second member 50 are not necessarily connected. The first member 10 and the second member 50 can be individually prepared in a separated state.

Next, a procedure for storing the microneedle array 40 in the storage container 1 will be described with reference to FIGS. 4 and 5.

Figure 4:
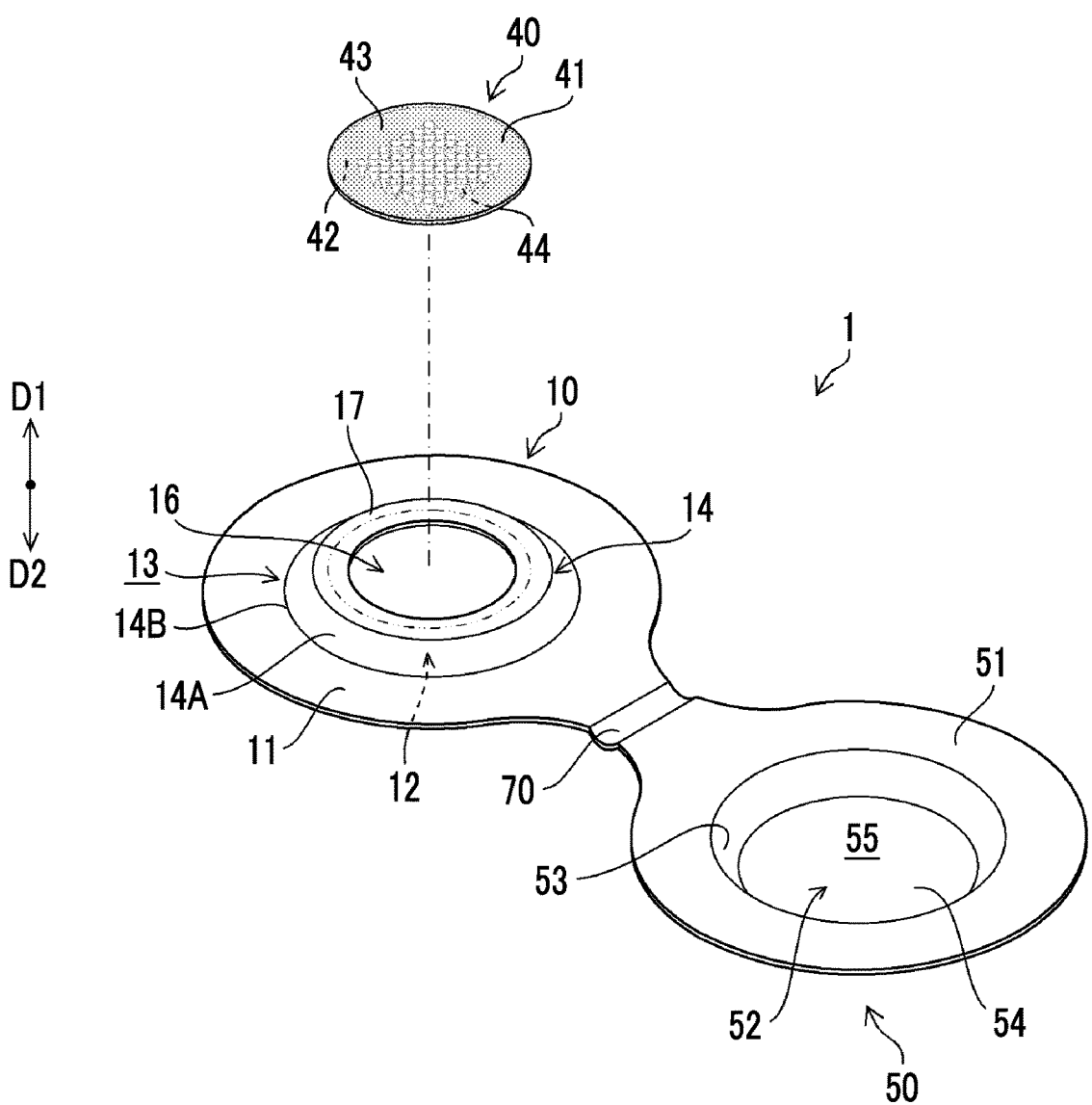
FIG. 4 is a perspective view illustrating the microneedle array and the storage container.

As illustrated in FIGS. 4 and 5 (105A), the first member 10 is prepared in a state in which the second opening 16 of the support portion 13 is directed in the first direction D1 (upward direction). The second member 50 connected to the first member 10 through the hinge portion 70 is prepared in a state in which the opening 52 is directed in the first direction D1. The first member 10 is installed on a jig (not illustrated) or the like.

The second surface 43 of the sheet 41 of the microneedle array 40 is adsorbed from above the sheet 41 by, for example, an adsorption pad (not illustrated). The needles 44 of the microneedle array 40 are directed downward, and the needles 44 and the second opening 16 of the support portion 13 are arranged to oppose each other. The plurality of needles 44 are positioned at a position where the needles 44 are not in contact with the edge portion 17 so as to fit inside the second opening 16.

By adsorbing the second surface 43 of the sheet 41, the microneedle array 40 can be handled without damaging the needles 44.

As illustrated in FIG. 5, the first opening 12 of the first member 10 is blocked by a lid member 80 having a sheet shape. The first flat portion 11 of the first member 10 and the lid member 80 are bonded by applying, for example, heat or ultrasonic waves. Similarly to the lid member 80 and the storage container 1, it is formed of, for example, a polyethylene resin, a polypropylene resin, or a mixture thereof.

As illustrated in 105B, the microneedle array 40 is moved toward the first member 10. The microneedle array 40 is placed on the edge portion 17 of the support portion 13. The outer peripheral portion 45 of the microneedle array 40 is supported by the support portion 13. In the embodiment, the edge portion 17 of the support member 14 supports the outer peripheral portion 45 of the microneedle array 40.

A height h of the support portion 13 is set to be larger than the height of the needles 44. The needles 44 do not protrude from the first opening 12 in a state in which the outer peripheral portion 45 of the microneedle array 40 is supported by the support portion 13. The height h is a distance from the first opening 12 to the tip of the support portion 13.

The second opening 16 of the first member 10 has an area which is smaller than the sheet 41 of the microneedle array 40 and larger than the region where the plurality of needles 44 are arranged. The plurality of needles 44 are arranged inside the second opening 16 so that the support portion 13 is not in contact with the needles 44. Further, the edge portion 17 of the support portion 13 is capable of reliably holding the outer peripheral portion 45 of the microneedle array 40.

The plurality of needles 44 are held in a space defined by the lid member 80 and the support portion 13, and the needles 44 are protected by the first member 10 and the lid member 80 until the needles 44 puncture the skin.

Next, as indicated by the arrows, the second member 50 is bent toward the first member 10 with the hinge portion 70 as a starting point.

The second member 50 is superimposed on the first member 10 as illustrated in 105C. The support portion 13 of the first member 10 and the microneedle array 40 are stored in the depression 55 of the second member 50 from a side of the second opening 16. The base 54 of the second member 50 is in contact with the second surface 43 of the microneedle array 40. The microneedle array 40 is interposed between the base 54 of the second member 50 and the edge portion 17 of the support portion 13 in the vertical direction.

The first flat portion 11 of the first member 10 and the second flat portion 51 of the second member 50 are superimposed, and the first flat portion 11 and the second flat portion 51 are bonded by heat, an adhesive, ultrasonic waves, or the like. The microneedle array 40 is fixed by the first member 10 and the second member 50.

A microneedle unit 100 including the storage container 1 and the microneedle array 40 is produced.

The microneedle array 40 is fixed by the first member 10 and the second member 50 without using an adhesive so that the microneedle array 40 is stored in the storage container 1. Therefore, it is possible to avoid the problem of deterioration of the drug due to the stability of the adhesive.

At the time of storage of the microneedle array 40 in the storage container 1, a force is not applied to the microneedle array 40 as in a case where the microneedle array 40 is fitted, and thus the damage to the microneedle array 40 can be avoided.

As illustrated in FIGS. 4 and 5, the support portion 13 has rigidity because the support portion 13 is formed of the inclined surface 14A that is three-dimensionally molded in a conical shape. The microneedle array 40 can be stably protected.

In FIG. 5, the case where the microneedle array 40 is supported by the support portion 13 of the first member 10, the second member 50 is bent, and the second member 50 is superimposed on the first member 10 has been described. However, the present invention is not limited to this method.

For example, first, the microneedle array 40 is placed on the base 54 by allowing the second surface 43 of the microneedle array 40 to face the base 54. Next, the first member 10 is bent toward the second member 50 with the hinge portion 70 as a starting point. The first member 10 is superimposed on the second member 50. The support portion 13 is stored in the depression 55 so that the outer peripheral portion 45 of the microneedle array 40 can be supported by the edge portion 17 of the support portion 13 of the first member 10. The edge portion 17 of the support portion 13 is brought into contact with the outer peripheral portion 45 of the microneedle array 40. The microneedle array 40 is interposed between the edge portion 17 of the support portion 13 and the base 54 of the second member 50 in the vertical direction. Next, the first flat portion 11 of the first member 10 and the second flat portion 51 of the second member 50 are bonded by heat, an adhesive, ultrasonic waves, or the like. The microneedle array 40 is fixed by the first member 10 and the second member 50. A microneedle unit 100 including the storage container 1 and the microneedle array 40 is produced.

In FIGS. 2 to 5, the case where the support portion 13 of the first member 10 is formed of the single annular support member 14 has been described. The shape of the support portion 13 is not limited thereto. Other shapes of the support portion 13 will be described with reference to FIGS. 6 and 9.

Figure 6:
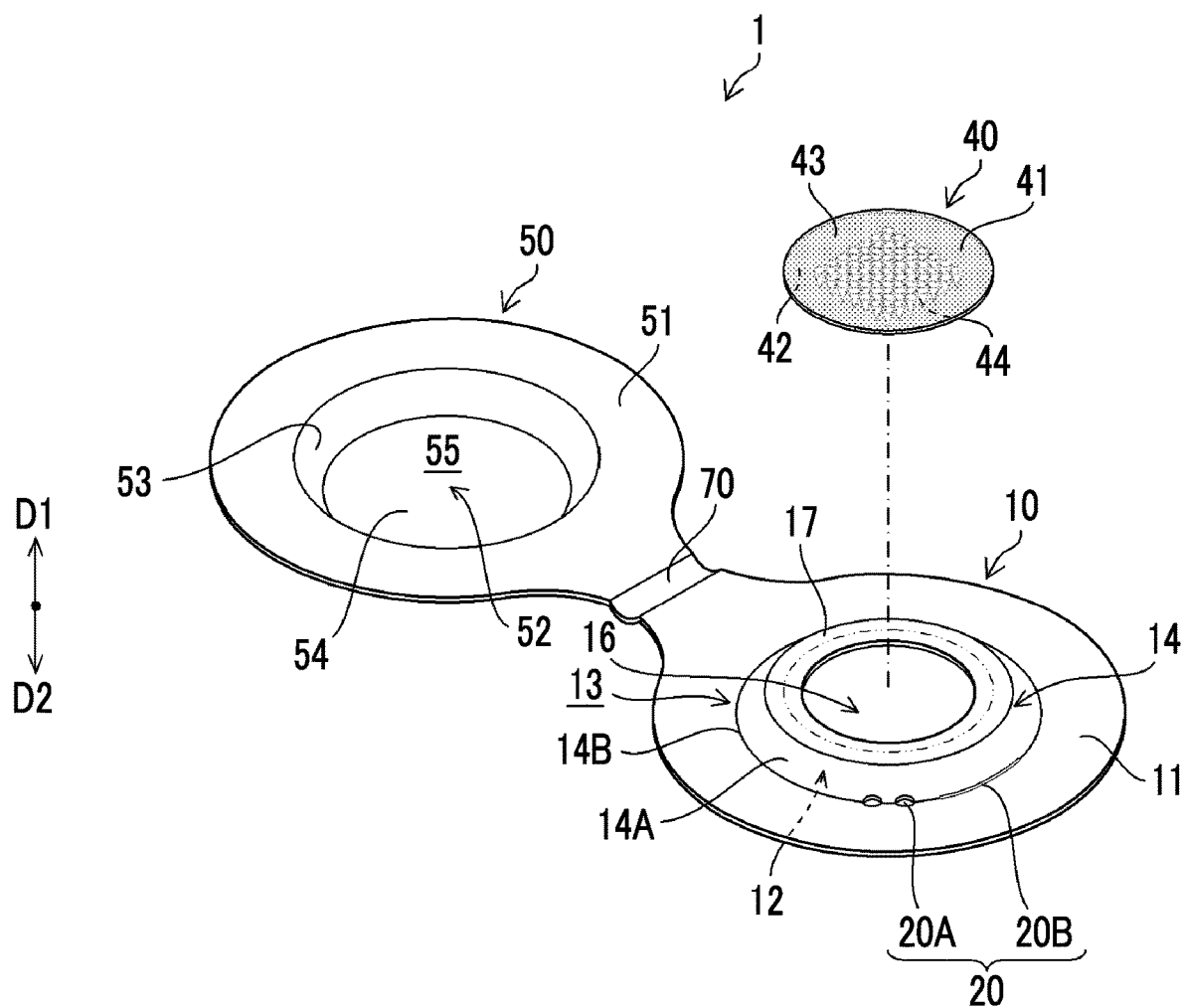
FIG. 6 is an explanatory view for explaining the shape of another support portion.

As illustrated in FIG. 6, a penetrating portion 20 can be provided at the rising portion 14B (a so-called root portion of the support portion 13) formed of the first flat portion 11 and the support portion 13. The penetrating portion 20 penetrates the first member 10 in the thickness direction of the first member 10. The shape of the penetrating portion 20 is not particularly limited and may be, for example, a through-hole 20A or a slit hole 20B. A through-hole 20A has a shape in which a part of the first member 10 is missing and the first member 10 is hollowed out in a plan view of the first member 10. The through-hole 20A has, for example, a circular shape, an elliptical shape, or the like in a plan view. The shape of the through-hole 20A is not limited.

The slit hole 20B is a notch formed in the first member 10 and has a linear shape in a plan view of the first member 10. The first member 10 is separated at the position of the slit hole 20B. The penetrating portion 20 is capable of adjusting the force at the time of inversion of the first member 10.

As illustrated in 107A and 107B of FIG. 7, the support portion 13 is of a plurality of the support members 14 separated by a plurality of notches 14C. The support member 14 rises in the upward direction (the first direction D1) with respect to the first flat portion 11. The support member 14 has a constricted portion 14D formed of the first flat portion 11 and the rising portion 14B. The constricted portion 14D is a narrow portion in the support member 14.

As illustrated in FIG. 7, the second opening 16 is defined by the edge portions 17 of the plurality of support members 14. The edge portion 17 is a tip of the support member 14. Further, the first opening 12 is defined by the rising portion 14B of the support member 14.

As illustrated in 107A, the notch 14C extends to the first flat portion 11 beyond the support member 14. The width of the notch 14C is larger than the distance between the support members 14 in the region of the first flat portion 11. As illustrated in 107A, the notch 14C has a substantially triangular shape in a plan view, with the space between the edge portions 17 of the support member 14 as a vertex and with the portion reaching the first flat portion 11 as a bottom side. As a result, a portion with a narrow width is formed in the first flat portion 11.

At the time of inversion of the support portion 13 of the first member 10 illustrated in FIG. 7, the support portion 13 is bent not by the rising portion 14B but by a bent portion 14E indicated by a dashed line of the first flat portion 11 in the downward direction (the second direction D2). As illustrated in FIG. 8, the bent portion 14E is a thin portion formed on the first flat portion 11, and the bent portion 14E is likely to be bent. The support portion 13 can be stably inverted.

In the support portion 13 of the first member 10, the rising portion 14B is different from the bent portion 14E. The support portion 13 of the first member 10 can adjust the positions of the rising portion 14B and the bent part.

By separating the edge portion 17 of the support member 14 by the notch 14C, it is possible to prevent occurrence of deformation that affects the puncture due to buckling of the support portion 13 during the inverse deformation.

As illustrated in 108A and 108B of FIG. 8, the support portion 13 is formed of a plurality of the support members 14 separated by a plurality of the notches 14C. The support member 14 rises in the upward direction (the first direction D1) with respect to the first flat portion 11. As illustrated in FIG. 8, the second opening 16 is defined by the edge portions 17 of the plurality of support members 14.

As illustrated in 108A, the support member 14 has a rectangular shape in a plan view. The support member 14 has a substantially constant width from the rising portion 14B to the edge portion 17. Similar to FIG. 7, the first opening 12 is defined by the rising portions 14B of the support members 14.

As illustrated in 109A and 109B of FIG. 9, the support portion 13 is formed of a plurality of the support members 14 separated by a plurality of the notches 14C. The support member 14 rises in the upward direction (the first direction D1) with respect to the first flat portion 11. The number of the support members 14 in FIG. 9 is smaller than the number of the support members 14 in FIG. 8. The notch 14C in FIG. 9 is larger than the notch 14C in FIG. 8. As illustrated in FIG. 9, the second opening 16 is defined by the edge portions 17 of the plurality of support members 14.

As illustrated in 109A, the support member 14 has a substantially rectangular shape in a plan view. The support member 14 has a substantially constant width from the rising portion 14B to the edge portion 17. Meanwhile, the edge portion 17 of the support member 14 has a chamfered arc shape at a corner in a plan view. Similar to FIG. 7, the first opening 12 is defined by the rising portions 14B of the support members 14.

As illustrated in FIGS. 7 to 9, the shape of the support portion 13 can be appropriately determined based on the required function.

Next, a storage container group will be described with reference to FIG. 10. As illustrated in 110A of FIG. 10, the storage container 1 is formed such that the first member 10 and the second member 50 are connected to each other through the hinge portion 70. In this manner, one storage container 1 is prepared.

A plurality of the storage containers 1 are prepared. The first members 10 of the adjacent storage containers 1 are connected to each other, and the second members 50 are connected to each other so that the plurality of storage containers 1 are arranged in one direction (X direction). One storage container group 200 surrounded by a two-dot chain line is prepared. By setting the plurality of storage containers 1 as one storage container group 200, the storage containers 1 are easily handled.

Figure 10:
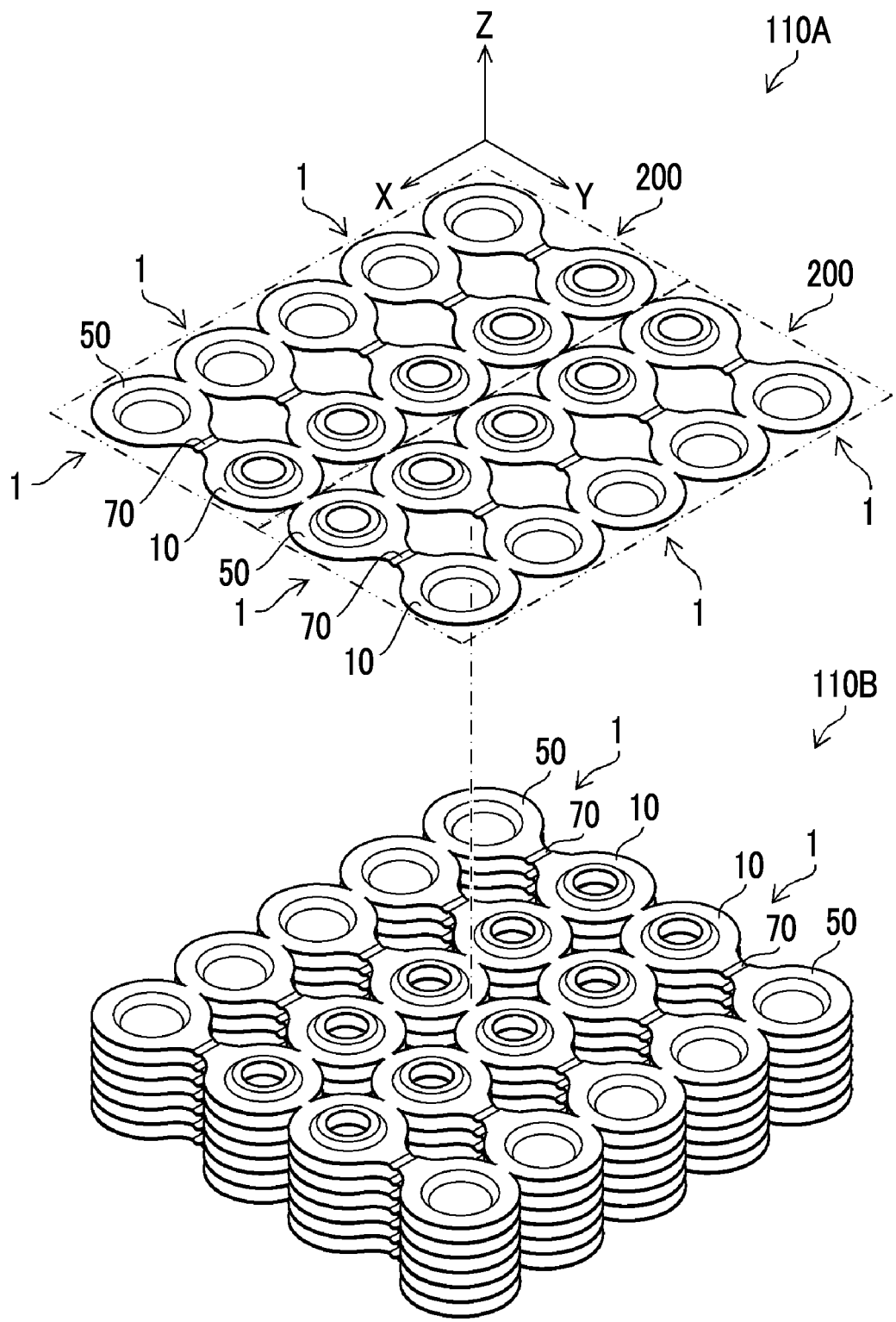
FIG. 10 is a perspective view for explaining a storage container group.

In FIG. 10, a plurality of the storage container groups 200 are prepared, and the first members 10 of the plurality of storage container groups 200 are connected to each other. Two storage container groups 200 form a larger storage container group 200. Two storage container groups 200 become adjacent to each other and are connected to each other in a Y direction. As the number of storage containers 1 included in the storage container group 200 increases, handling of the storage container 1, for example, transport of the storage containers 1 becomes easier. As illustrated in 110B of FIG. 10, the storage container groups 200 can be stacked in a Z direction.

Figure 11:
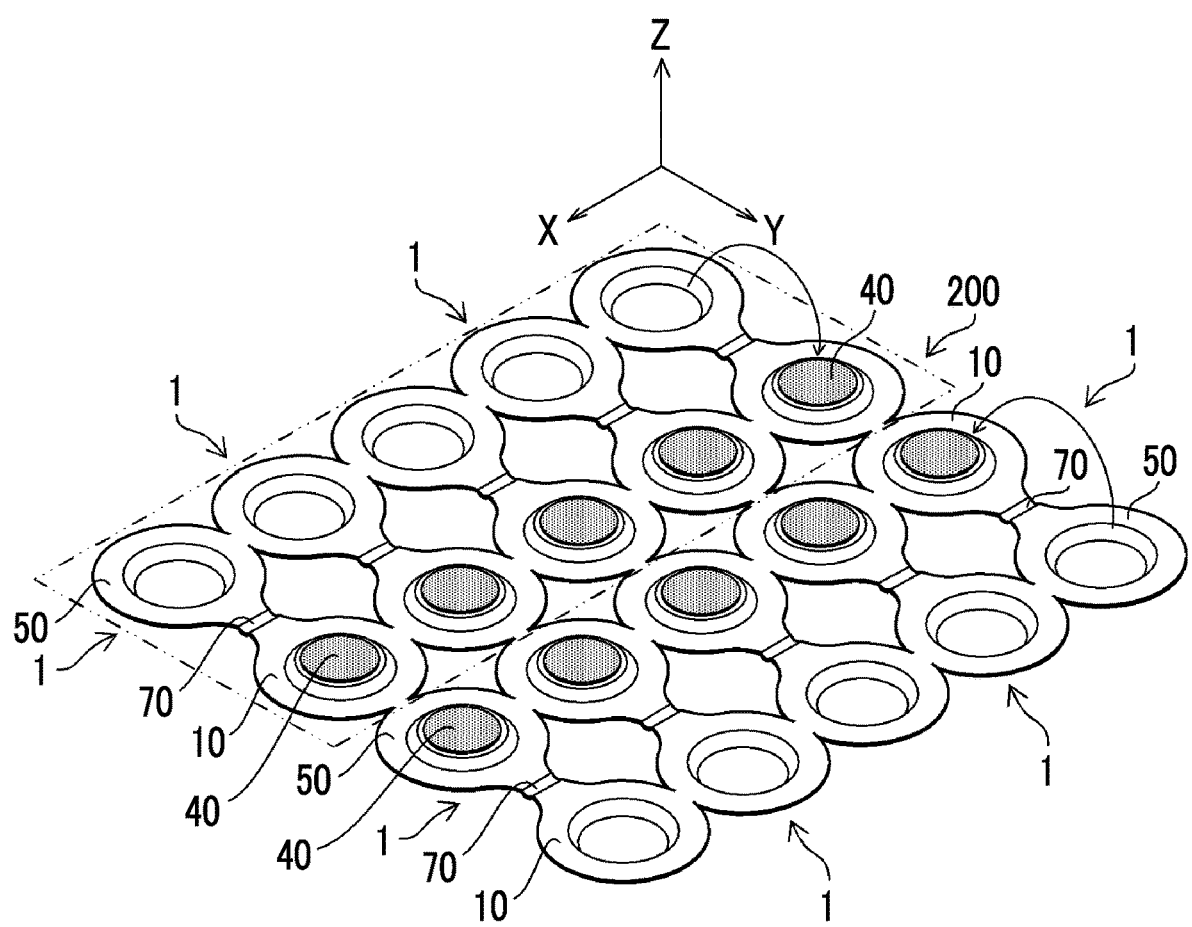
FIG. 11 is a perspective view for explaining the storage container group.

The storage container groups 200 stacked in the Z direction are transported to, for example, a sterile room where the microneedle array 40 is produced. In the sterile room, as illustrated in FIG. 11, one storage container group 200 is taken out from the plurality of storage container groups 200 stacked in the Z direction. The microneedle array 40 is placed on each of the edge portions 17 of the first member 10 of the storage container 1 constituting the storage container group 200. Next, as indicated by the arrows, the second member 50 is bent toward the first member 10 with the hinge portion 70 as a starting point. The second member 50 is superimposed on the first member 10.

According to the storage container group 200 of the embodiment, the plurality of storage containers 1 are integrally formed, and the lid member 80 is bonded to the storage container 1. The assembly of the storage containers 1 included in the storage container group 200 can be completed before the storage containers 1 are carried into the sterile room. In the sterile room, only a step of storing the microneedle array 40 in the storage container 1 is performed. In the step of the storing, as illustrated in FIG. 5, the microneedle array 40 is placed on the support portion 13 of the first member 10, and the second member 50 is bent toward the first member 10 so that the second member 50 is superimposed on the first member 10, and the first member 10 and the second member 50 are bonded to each other. It is not necessary to assemble the storage container 1 in the sterile room. Since the plurality of storage containers 1 are integrally formed, the number of components of the storage container 1 to be transported to the sterile room can be reduced. In a case where the first member 10 and the second member 50 are bonded to each other, the microneedle array 40 is stored in the storage container 1 in a sterile state. Thereafter, the storage container group 200 is taken out of the sterile room, and the storage container group 200 can be separated into the individual storage containers 1. Further, an adhesive or adhesive tape (medical tape) is prepared at a portion of the storage container 1 that comes into contact with the skin.

Next, a procedure for puncturing the microneedle array 40 using the microneedle unit 100 will be described with reference to FIG. 12.

In a case where a skin S is punctured by the microneedle array 40, first, the lid member 80 is peeled off from the microneedle unit 100. The first opening 12 of the first member 10 of the storage container 1 is opened. The needles 44 of the microneedle array 40 are exposed from the first opening 12. Until the microneedle unit 100 is used, the microneedle array 40 is protected by the storage container 1 and the lid member 80.

As illustrated in 112A of FIG. 12, the storage container 1 is positioned on the skin S. The first opening 12 of the first member 10 is positioned toward the skin S, and the needles 44 of the microneedle array 40 are allowed to face the skin S.

The support portion 13 of the first member 10 is formed of the single support member 14. The support member 14 has an inclined surface 14A whose diameter is reduced, which rises from the first flat portion 11 in the first direction D1 from the rising portion 14B.

A force in the direction of the first member 10 (the second direction D2) is applied to the second member 50 by a finger or the like in a state in which the second member 50 is superimposed on the first member 10.

It is preferable that the first flat portion 11 of the first member 10 preferably has an adhesive or adhesive tape on a surface that comes into contact with the skin S. The storage container 1 can be attached to the skin, and unintentional movement of the storage container 1 from the skin S can be prevented. Even in a case where the first flat portion 11 does not have an adhesive, the skin S is coated with an adhesive or an adhesive is attached to the skin S so that the storage container 1 is attached to the skin S using the adhesive. Further, another member (medical tape) or the like is attached from above the storage container 1, the storage container 1 can be attached to the skin S.

As illustrated in 112B of FIG. 12, the second member 50 is deformed by the applied force, and the second member 50 presses the microneedle array 40 against the skin S. The first member 10 supporting the microneedle array 40 is deformed toward the skin S. The second member 50 is deformed until the base 54 moves to the opposite side with respect to the second flat portion 51. The base 54 and the side wall portion 53 are inverted with respect to the second flat portion 51. The inversion means that the base 54 and the side wall portion 53 change from a shape of a projection facing the first direction D1 to a shape of a depression (also referred to as a shape of a projection facing the second direction D2) with respect to the second flat portion 51.

The support portion 13 of the first member 10 is deformed until the second opening 16 moves to the opposite side with respect to the first flat portion 11. The support member 14 constituting the support portion 13 is bent at the rising portion 14B, and the support portion 13 is inverted with respect to the first flat portion 11. The inversion means that the support portion 13 changes from a shape of a projection facing the first direction D1 with respect to the first flat portion 11 to a shape of a depression in which the first opening 12 faces the first direction D1 (a shape of a projection in which the inverted inclined surface 14A and the second opening 16 face the second direction D2).

The needles 44 of the microneedle array 40 protrude from the first member 10, and the skin S is punctured by the needles 44.

As illustrated in 112B, the second member 50 maintains the deformed shape even after the force is removed. After the puncture, the second member 50 can keep pressing the microneedle array 40 toward the skin S until the drug of the microneedle array 40 is administered without pressing with a finger or the like.

As the first member 10 and the second member 50, a material that is deformed at the time of application of the force and is capable of maintaining the deformed shape is selected. The material is determined in consideration of the thickness of the material to be used, the magnitude of the external force required for the deformation, and the like.

Since the second member 50 forms the exterior of the storage container 1, it is preferable that the thickness thereof is relatively large from the viewpoint of protection of the microneedle array 40. However, in a case where the thickness thereof is extremely large, the force at the time of deformation increases. The thickness of the second member 50 is determined from the viewpoint of protection and deformation.

The first member 10 may have a thickness with a strength of supporting the microneedle array 40. In order to facilitate the deformation of the first member 10 and reduce the force applied by a finger or the like, it is preferable that the thickness is relatively small. Therefore, it is preferable that the thickness of the first member 10 is smaller than the thickness of the second member 50.

Figure 13:
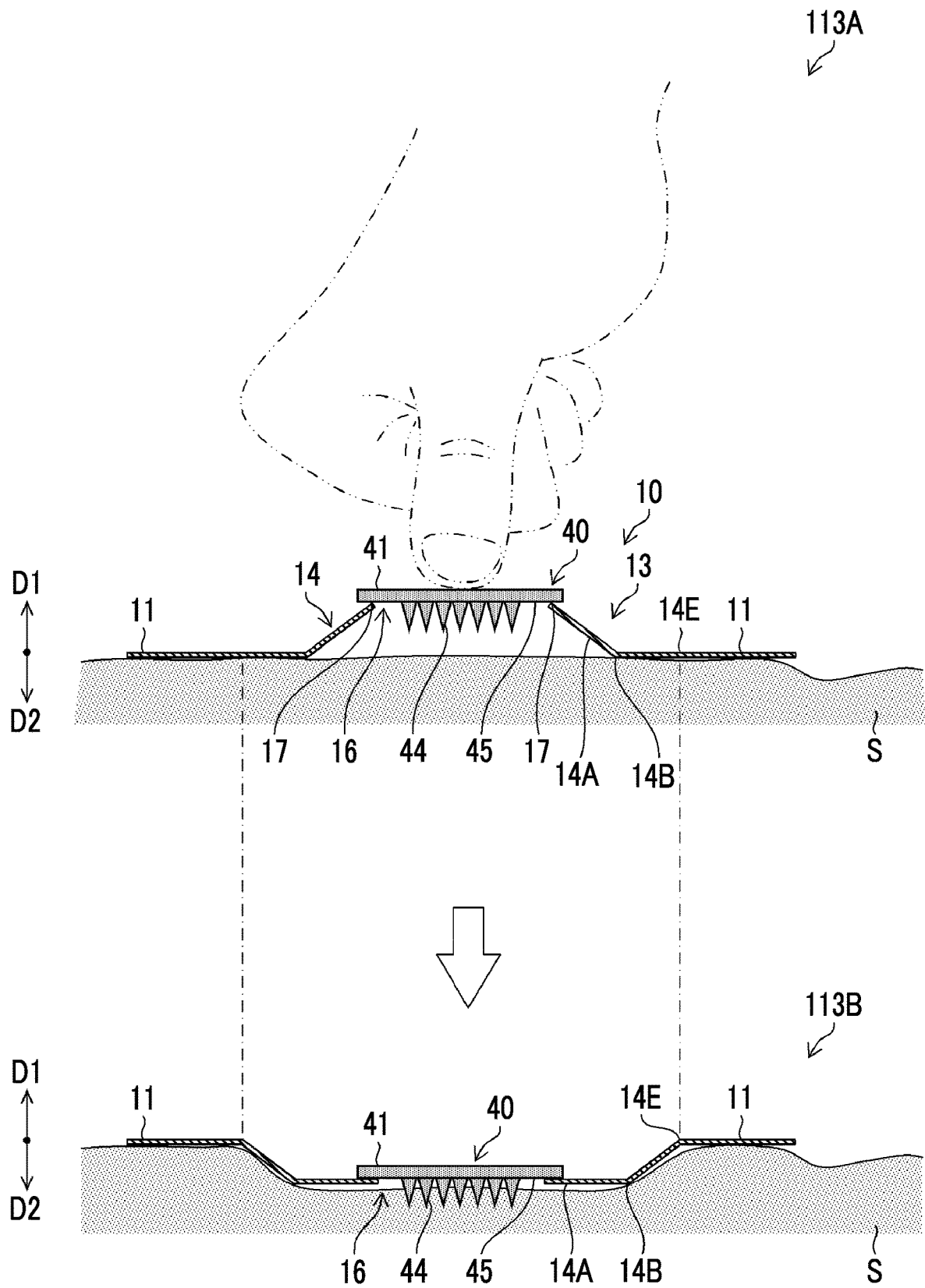
FIG. 13 is an explanatory view illustrating a procedure for puncturing the microneedle array.

Next, a procedure for puncturing the microneedle array 40 using a microneedle unit 100 (not illustrated) different from the microneedle unit used for the puncture illustrated in FIG. 12 will be described with reference to FIG. 13. The same configurations as those in FIG. 12 are denoted by the same reference numerals and the description thereof will not be provided. In FIG. 13, the second member 50 of the storage container 1 is omitted in order to facilitate the understanding.

The storage container 1 is positioned on the skin S as illustrated in 113A of FIG. 13. The first opening 12 of the first member 10 is positioned toward the skin S, and the needles 44 of the microneedle array 40 are allowed to face the skin S.

The support portion 13 of the first member 10 is formed of the single support member 14. The support member 14 has an inclined surface 14A whose diameter is reduced, which rises from the first flat portion 11 in the first direction D1 from the rising portion 14B. The first flat portion 11 of the first member 10 is provided with a bent portion 14E. The inclined surface 14A is inclined with respect to the puncture surface of the skin S. A force in the direction of the first member 10 (the second direction D2) is applied to the second member 50 by a finger or the like in a state in which the second member 50 is superimposed on the first member 10.

As illustrated in 113B of FIG. 13, the second member 50 is deformed by the applied force, and the second member 50 presses the microneedle array 40 against the skin S. The first member 10 supporting the microneedle array 40 is deformed toward the skin S. In the second member 50, the base 54 and the side wall portion 53 are inverted with respect to the second flat portion 51.

The support portion 13 of the first member 10 is deformed until the second opening 16 moves to the opposite side with respect to the first flat portion 11. The support member 14 constituting the support portion 13 is bent at the bent portion 14E, and the support portion 13 is inverted with respect to the first flat portion 11. The support member 14 has a shape of a depression in which the opening defined by the bent portion 14E faces the first direction D1 (a shape of a projection in which the second opening 16 faces the second direction D2). After the inversion, the support member 14 forms an inclined surface having a shape of a projection in which a part of the first flat portion 11 faces the second direction D2.

As illustrated in 113B, the support member 14 is bent at the bent portion 14E so that the inclined surface 14A becomes parallel to the puncture surface of the skin S.

Since the inclined surface 14A flattens the puncture surface, the needles 44 of the microneedle array 40 can easily puncture the skin S.

Next, a procedure for puncturing the microneedle array 40 using a microneedle unit 100 different from the microneedle unit used for the puncture illustrated in FIG. 12 will be described with reference to FIG. 14. The same configurations as those in FIG. 12 are denoted by the same reference numerals and the description thereof will not be provided.

Figure 14:
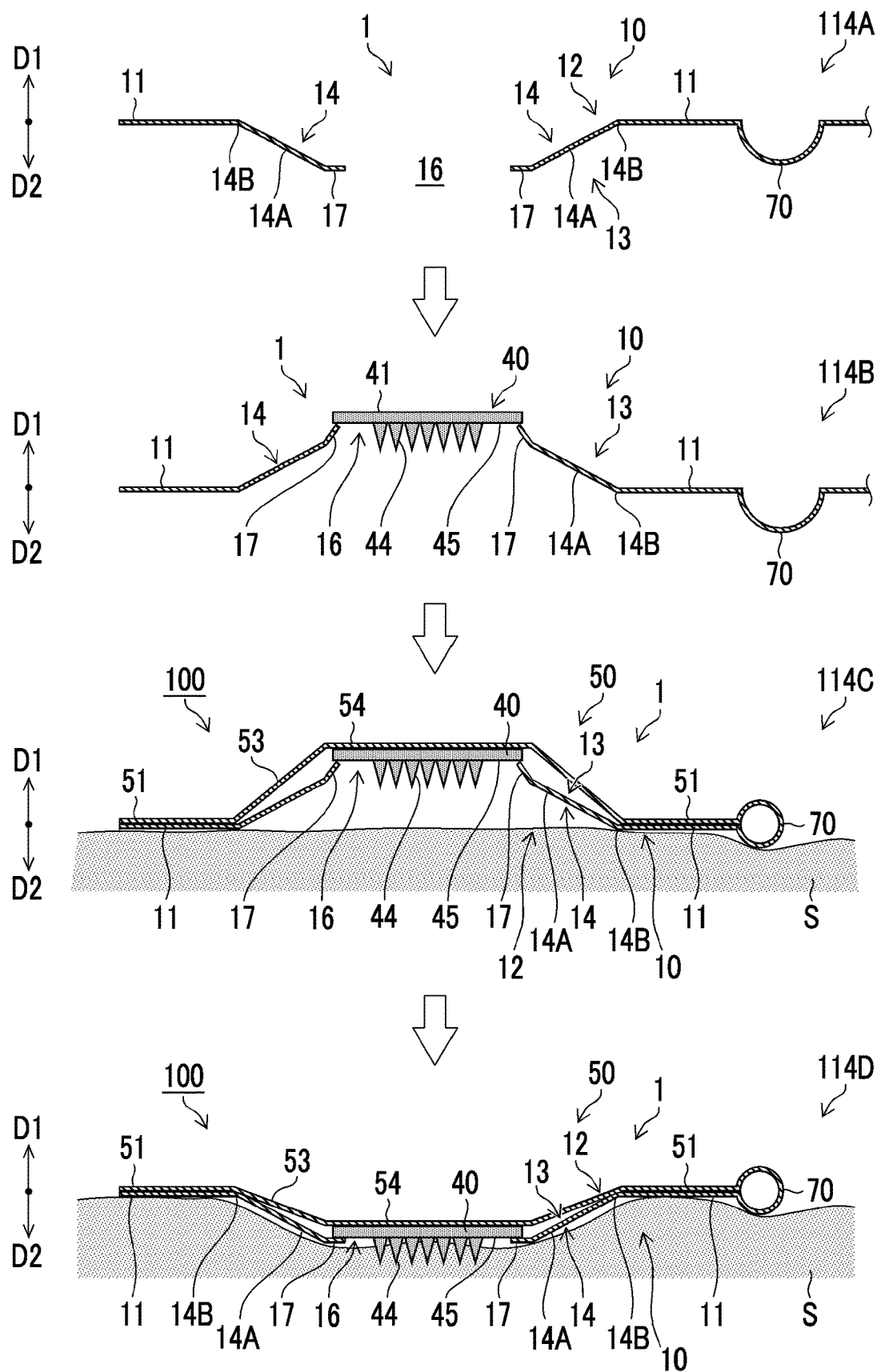
FIG. 14 is an explanatory view illustrating a procedure for puncturing the microneedle array.

As illustrated in 114A of FIG. 14, the first member 10 of the storage container 1 is prepared. The support member 14 constituting the support portion 13 of the first member 10 is raised in the second direction D2 which is one direction in the reference state. The second opening 16 defined by the inclined surface 14A and the edge portion 17 face the second direction D2. The shape of the support portion 13 is stable in this state, and the support portion 13 enters the reference state.

As illustrated in 114B, the support portion 13 is in an inverted state raised in the first direction D1, which is one direction opposite to the other direction, and supports the microneedle array 40 in this inverted state. The outer peripheral portion 45 of the microneedle array 40 is supported by the edge portion 17 of the support portion 13. Subsequently, the second member 50 is superimposed on the first member 10.

The storage container 1 is positioned on the skin S as illustrated in 114C. The first opening 12 of the first member 10 is positioned toward the skin S, and the needles 44 of the microneedle array 40 are allowed to face the skin S. A force in the direction of the first member 10 (the second direction D2) is applied to the second member 50 by a finger or the like in a state in which the second member 50 is superimposed on the first member 10.

As illustrated in 114D of FIG. 14, the second member 50 is deformed by the applied force, and the second member 50 presses the microneedle array 40 against the skin S. The first member 10 supporting the microneedle array 40 is deformed toward the skin S. In the second member 50, the base 54 and the side wall portion 53 are inverted with respect to the second flat portion 51.

The support member 14 constituting the support portion 13 is bent at the rising portion 14B, and the support portion 13 is inverted with respect to the first flat portion 11. The support portion 13 returns to the reference state that is stable in shape. At the time of puncture of the microneedle array 40, the support portion 13 can be inverted with a small force. Further, since the support portion 13 does not separate the microneedle array 40 from the skin S, the needles 44 of the microneedle array 40 can stably puncture the skin S. Further, the edge portion 17 of the support portion 13 becomes a surface that is reliably parallel to the skin S at the time of puncture, and the needles 44 easily puncture the skin.

Next, a storage container in another form and another puncturing method will be described with reference to FIGS. 15 and 16. The same configurations as those in FIG. 5 are denoted by the same reference numerals and the description thereof will not be provided. As illustrated in 115A of FIG. 15, the first member 10 is prepared in a state where the second opening 16 of the support portion 13 is allowed to face the first direction D1 (upward direction). The first member 10 is installed on a jig (not illustrated) or the like. The second member 50 connected to the first member 10 through the hinge portion 70 is prepared in a state in which the opening 52 is directed in the first direction D1.

As illustrated in 115A, in the second member 50, the shape of the side wall portion 53 rising from the opening 52 of the second flat portion 51 is different from the shape of the second member 50 of the storage container 1 illustrated in FIG. 5.

The side wall portion 53 is orthogonal to the second flat portion 51 and comprises a first portion 53A which extends in the second direction D2, a second portion 53B which is orthogonal to the first portion 53A and extends inward, a third portion 53C which is orthogonal to the second portion 53B and extends in the second direction D2, and a fourth portion 53D which is continuous with the third portion 53C and whose diameter is reduced in the second direction D2. The base 54 is connected to the side wall portion 53.

A depression 55 defined by the side wall portion 53 and the base 54 is formed in the second member 50. The depression 55 has a first depression 55A and a second depression 55B. The first depression 55A is defined by the first portion 53A and the second portion 53B of the side wall portion 53. The second depression 55B is defined by the third portion 53C and the fourth portion 53D of the side wall portion 53, and the base 54.

A pusher 60 along the shape of the second depression 55B is stored in the second depression 55B. The pusher 60 is made of a resin and has a shape formed by combining a cylinder and a truncated cone. The pusher 60 has two cylinders having different diameters, and the side of the microneedle array 40 may have a two-stage cylindrical shape with a large diameter. The shape of the pusher 60 is not particularly limited as long as the microneedle array 40 can stably puncture the skin. The pusher 60 is fixed to the base 54 by performing bonding, welding, fitting, or the like.

The microneedle array 40 is moved toward the first member 10 as illustrated in 115B. The microneedle array 40 is placed on the edge portion 17 of the support portion 13. The outer peripheral portion 45 of the microneedle array 40 is supported by the support portion 13. In the embodiment, the edge portion 17 of the support member 14 supports the outer peripheral portion 45 of the microneedle array 40.

Next, as indicated by the arrows, the second member 50 in which the pusher 60 is stored in the depression 55 is bent toward the first member 10 with the hinge portion 70 as a starting point.

As illustrated in 115C, the second member 50 is superimposed on the first member 10. The support portion 13 of the first member 10 and the microneedle array 40 are stored in the second depression 55B of the depression 55 of the second member 50 from a side of the second opening 16. The pusher 60 is brought into contact with the second surface 43 of the microneedle array 40. The microneedle array 40 is interposed between the pusher 60 and the edge portion 17 of the support portion 13 in the vertical direction.

The first flat portion 11 of the first member 10 and the second flat portion 51 of the second member 50 are superimposed, and the first flat portion 11 and the second flat portion 51 are bonded by heat, an adhesive, ultrasonic waves, or the like. The microneedle array 40 is fixed by the first member 10 and the second member 50. The microneedle unit 100 including the microneedle array 40 and the storage container 1 that stores the pusher 60 is produced.

Figure 15:
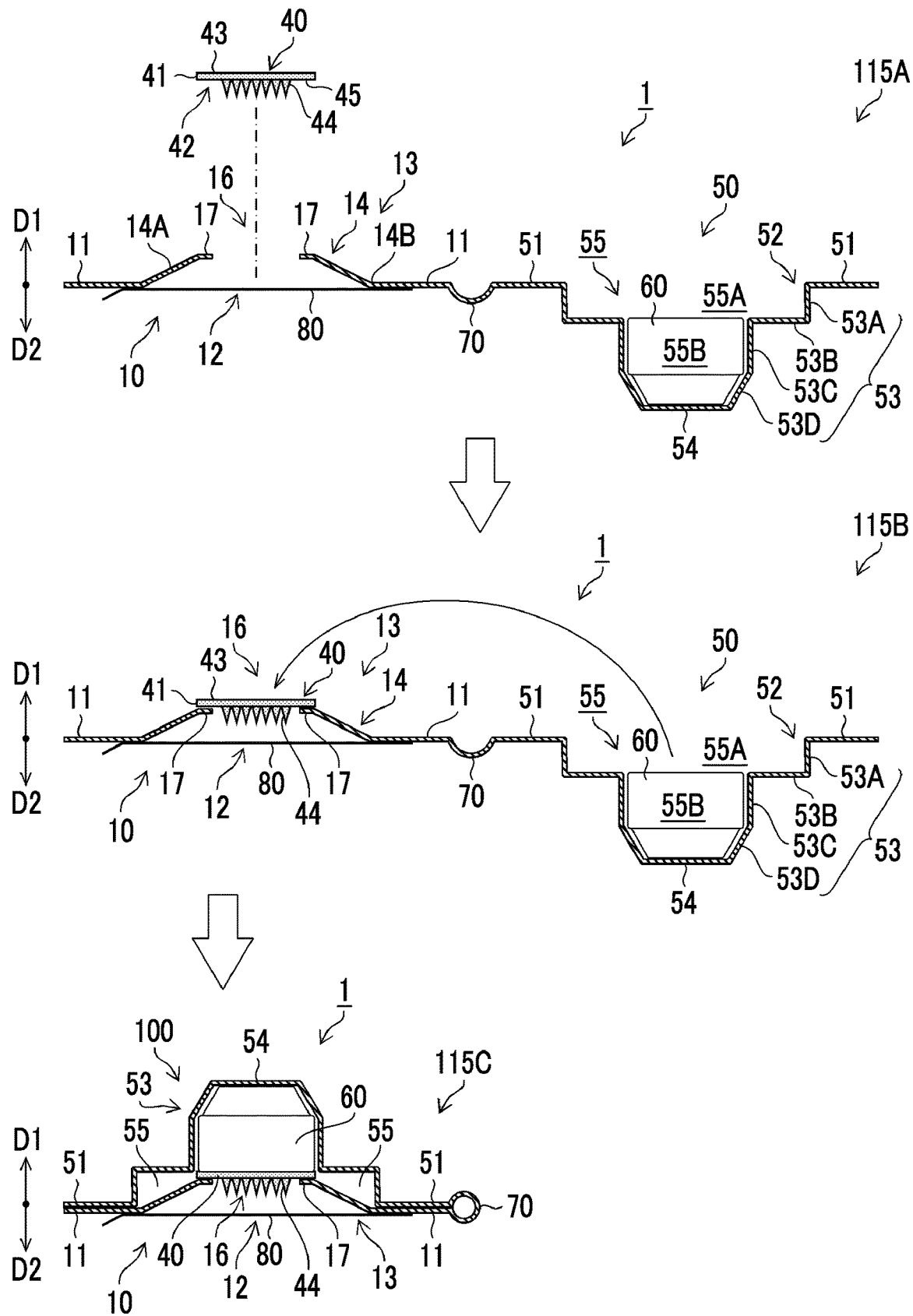
FIG. 15 is an explanatory view illustrating a procedure for storing the microneedle array in another storage container.

FIG. 15 illustrates the case where the microneedle array 40 is supported by the support portion 13 of the first member 10, the second member 50 is bent, and the second member 50 is superimposed on the first member 10. However, the present invention is not limited to this method.

Similar to another method described with reference to FIG. 5, the first member 10 can be bent toward the second member 50 with the hinge portion 70 as a starting point even in FIG. 15. First, the pusher 60 is placed in the second depression 55B of the second member 50. In this case, it is not necessary to bond the pusher 60 and the base 54 of the second member 50 to each other. Next, the microneedle array 40 is placed on the pusher 60 by allowing the second surface 43 of the microneedle array 40 to face the pusher 60.

Next, the first member 10 is bent toward the second member 50 with the hinge portion 70 as a starting point. The first member 10 is superimposed on the second member 50. The support portion 13 is stored in the first depression 55A so that the outer peripheral portion 45 of the microneedle array 40 can be supported by the edge portion 17 of the support portion 13 of the first member 10. The edge portion 17 of the support portion 13 is brought into contact with the outer peripheral portion 45 of the microneedle array 40. The microneedle array 40 is interposed between the edge portion 17 of the support portion 13 and the pusher 60 in the vertical direction. Next, the first flat portion 11 of the first member 10 and the second flat portion 51 of the second member 50 are bonded by heat, an adhesive, ultrasonic waves, or the like. The microneedle array 40 is fixed by the first member 10 and the second member 50. A microneedle unit 100 including the storage container 1 and the microneedle array 40 is produced.

The microneedle array 40 is fixed by the first member 10 and the second member 50 without using an adhesive so that the microneedle array 40 is stored in the storage container 1. Therefore, it is possible to avoid the problem of deterioration of the drug due to the stability of the adhesive.

At the time of storage of the microneedle array 40 in the storage container 1, a force is not applied to the microneedle array 40 as in a case where the microneedle array 40 is fitted, and thus the damage to the microneedle array 40 can be avoided.

Next, a procedure for puncturing the microneedle array 40 using the microneedle unit 100 illustrated in FIG. 15 will be described with reference to FIG. 16.

In a case where a skin S is punctured by the microneedle array 40, first, the lid member 80 is peeled off from the microneedle unit 100. The first opening 12 of the first member 10 of the storage container 1 is opened. The needles 44 of the microneedle array 40 are exposed from the first opening 12. Until the microneedle unit 100 is used, the microneedle array 40 is protected by the storage container 1 and the lid member 80.

Figure 16:
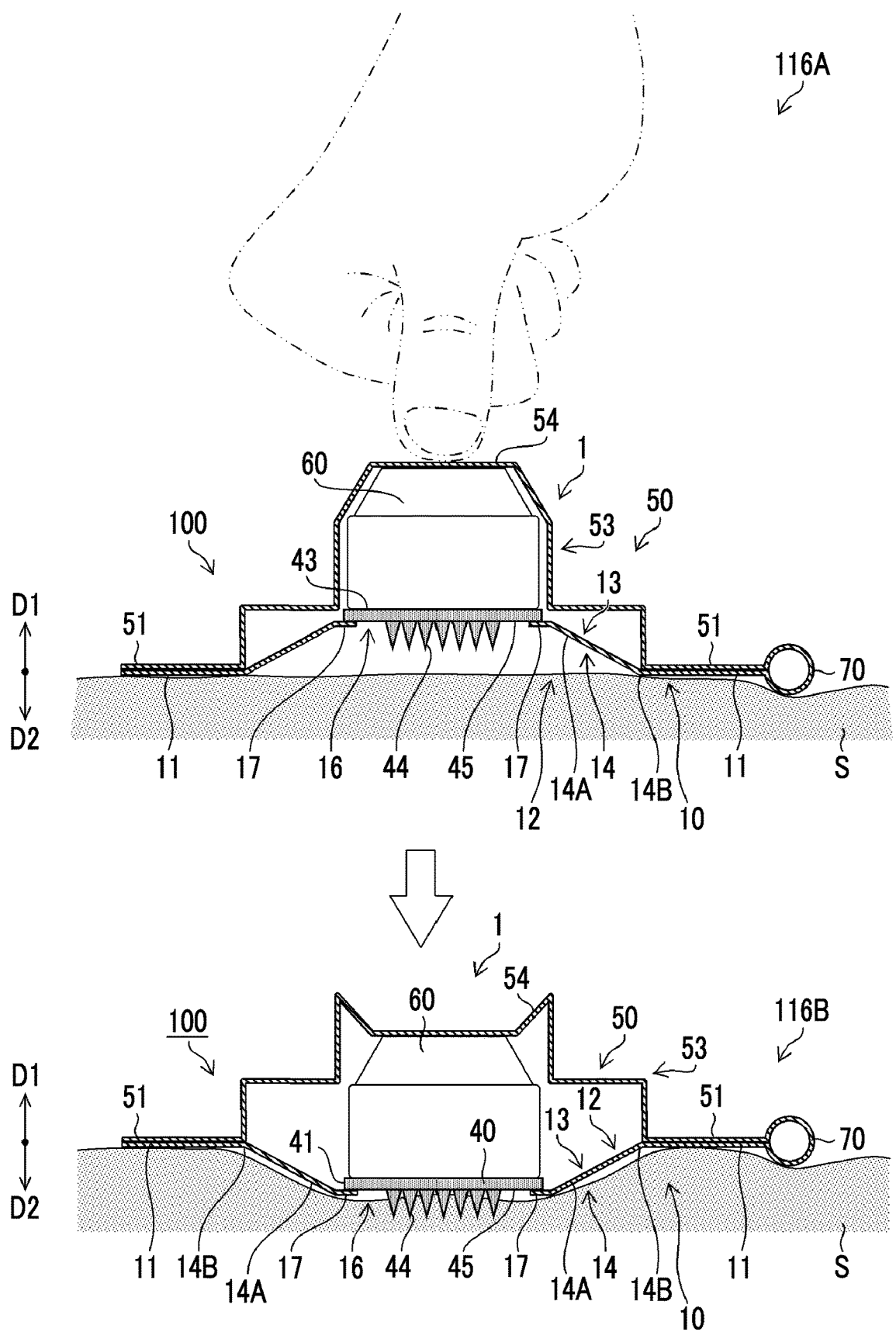
FIG. 16 is an explanatory view illustrating a procedure for puncturing the microneedle array stored in the storage container illustrated in FIG. 15.

The storage container 1 is positioned on the skin S as illustrated 116A of FIG. 16. The first opening 12 of the first member 10 is positioned toward the skin S, and the needles 44 of the microneedle array 40 are allowed to face the skin S.

The support portion 13 of the first member 10 is formed of the single support member 14. The support member 14 has an inclined surface 14A whose diameter is reduced, which rises from the first flat portion 11 in the first direction D1 from the rising portion 14B.

In a state in which the second member 50 is superimposed on the first member 10, a force directed in the direction of the first member 10 (the second direction D2) is applied to the second member 50 by a finger or the like and further transmitted to the pusher 60.

It is preferable that the first flat portion 11 of the first member 10 contains an adhesive or the like on a surface that comes into contact with the skin S.

As illustrated in 116B, the base 54 of the second member 50 is deformed by the applied force, and the pusher 60 presses the microneedle array 40 against the skin S. Due to the presence of the pusher 60, only the base 54 of the second member 50 is deformed in the second direction D2. The pusher 60 is pushed out from the second depression 55B by the applied force, and the pusher 60 presses the microneedle array 40 against the skin S. The first member 10 supporting the microneedle array 40 is deformed toward the skin S.

The support member 14 constituting the support portion 13 is bent at the rising portion 14B, and the support portion 13 is inverted with respect to the first flat portion 11.

The needles 44 of the microneedle array 40 protrude from the first member 10, and the skin S is punctured by the needles 44.

Since the microneedle array 40 is pressed through the pusher 60, the second surface 43 of the microneedle array 40 is evenly pressed. The needles 44 of the microneedle array 40 accurately puncture the skin S so that damage to the needles 44, for example, breaking or bending of the needles 44 can be prevented.

EXPLANATION OF REFERENCES

1: storage container
10: first member

11: first flat portion
12: first opening
13: support portion
14: support member
14A: inclined surface
14B: rising portion
14C: notch
14D: constricted portion
14E: bent portion
16: second opening
17: edge portion
20: penetrating portion
20A: through-hole
20B: slit hole
40: microneedle array
41: sheet
42: first surface
43: second surface
44: needle
45: outer peripheral portion
50: second member
51: second flat portion
52: opening
53: side wall portion
53A: first portion
53B: second portion
53C: third portion
53D: fourth portion
54: base
55: depression
55A: first depression
55B: second depression
60: pusher
70: hinge portion
80: lid member
100: microneedle unit
200: storage container group
D1: first direction
D2: second direction
S: skin
α: angle
β: angle

What is claimed is:

1. A storage container which stores a microneedle array including a sheet having a first surface and a second surface that oppose each other and a plurality of needles arranged on the first surface of the sheet, the storage container comprising:
a first member which includes a first flat portion in which a first opening is formed, and a support portion rising from a peripheral edge of the first opening and defining a second opening with an edge portion and in which an outer peripheral portion where the needles on the sheet of the microneedle array are not arranged is supported by the edge portion of the support portion while allowing the needles of the microneedle array to face the first opening; and
a second member which includes a second flat portion in which an opening is formed, a side wall portion rising from a periphery of the opening, and a base connected to the side wall portion and facing the opening and defines a depression with the side wall portion and the base and in which the support portion of the first member is stored in the depression from a side of the second opening by superimposing the second member on the first member, and the microneedle array is stored between the first member and the second member,
wherein the second member and the first member are deformed by applying a force in a direction of the first member to the second member in a state in which the second member is superimposed on the first member, and the needles of the microneedle array are allowed to protrude from the first member to puncture a skin.

2. The storage container according to claim 1,
wherein the second opening of the support portion has an area that is smaller than the sheet of the microneedle array and larger than a region where the plurality of needles are arranged.

3. The storage container according to claim 1,
wherein the first member and the second member are connected through a hinge portion.

4. The storage container according to claim 1,
wherein the first member and the second member have thicknesses different from each other.

5. The storage container according to claim 4,
wherein a thickness of the first member is smaller than a thickness of the second member.

6. The storage container according to claim 1,
wherein a thickness of the first member is in a range of 100 μm to 1000 μm, and
a thickness of the second member is in a range of 100 μm to 1000 μm.

7. The storage container according to claim 1,
wherein the first member includes a penetrating portion formed along a rising portion of the support portion.

8. The storage container according to claim 1,
wherein the support portion supports the microneedle array in an inversion state in which the support portion rises in one direction opposite to the other direction from a reference state in which the support portion rises in the other direction, and
the support portion is inverted and returns to the reference state upon application of the force to the second member.

9. The storage container according to claim 1,
wherein the support portion is formed of a plurality of support members which are separated from one another.

10. The storage container according to claim 9,
wherein the support member includes a constricted portion.

11. The storage container according to claim 1,
wherein the support portion has an inclined surface whose diameter is reduced in a rising direction and which is inclined with respect to a puncture surface, and
the inclined surface becomes parallel to the puncture surface in a case where the needles of the microneedle array are allowed to protrude from the first member to puncture the skin.

12. A microneedle unit comprising:
a microneedle array which includes a sheet having a first surface and a second surface that oppose each other and a plurality of needles arranged inside an outer peripheral portion of the first surface of the sheet; and
the storage container according to claim 1.

13. A storage container group comprising:
a plurality of the storage containers according to claim 1,
wherein the storage containers are arranged in one direction by connecting the first members to one another and connecting the second members to one another.

14. A storage container group comprising:
a plurality of the storage container groups according to claim 13, wherein the storage container groups are arranged by connecting the first members to one another or the second members to one another.

15. A method of producing a microneedle unit, comprising:
preparing a microneedle array which includes a sheet having a first surface and a second surface that oppose each other and a plurality of needles arranged inside an outer peripheral portion of the first surface of the sheet;
preparing a storage container which includes a first member including a first flat portion in which a first opening is formed and a support portion rising from a peripheral edge of the first opening in a first direction and defining a second opening with an edge portion, and a second member which includes a second flat portion in which an opening is formed, a side wall portion rising from a periphery of the opening, and a base connected to the side wall portion and facing the opening and defines a depression with the side wall portion and the base;
supporting the outer peripheral portion of the microneedle array with the edge portion of the support portion while allowing the needles of the microneedle array to face the first opening; and
storing the support portion of the first member and the microneedle array in the depression of the second member from a side of the second opening by superimposing the second member on the first member.

16. A method of producing a microneedle unit, comprising:
preparing a microneedle array which includes a sheet having a first surface and a second surface that oppose each other and a plurality of needles arranged inside an outer peripheral portion of the first surface of the sheet;
preparing a storage container which includes a first member including a first flat portion in which a first opening is formed and a support portion rising from a peripheral edge of the first opening in a first direction and defining a second opening with an edge portion, and a second member which includes a second flat portion in which an opening is formed, a side wall portion rising from a periphery of the opening, and a base connected to the side wall portion and facing the opening and defines a depression with the side wall portion and the base;
placing the microneedle array on the base while allowing the second surface of the microneedle array to face the base; and
storing the support portion in the depression by superimposing the first member on the second member so that the outer peripheral portion of the microneedle array is supported by the edge portion of the support portion.

* * * * *